(12) United States Patent
Murase et al.

(10) Patent No.: US 9,364,421 B2
(45) Date of Patent: Jun. 14, 2016

(54) HAIR COSMETIC

(71) Applicant: KOSE Corporation, Tokyo (JP)

(72) Inventors: Masatake Murase, Tokyo (JP); Yuji Masubuchi, Tokyo (JP)

(73) Assignee: KOSE CORPORATION, Tokyo (JP)

( * ) Notice: Subject to any disclaimer, the term of this patent is extended or adjusted under 35 U.S.C. 154(b) by 0 days.

(21) Appl. No.: 14/388,277

(22) PCT Filed: Mar. 28, 2013

(86) PCT No.: PCT/JP2013/002127
§ 371 (c)(1),
(2) Date: Sep. 26, 2014

(87) PCT Pub. No.: WO2013/145755
PCT Pub. Date: Oct. 3, 2013

(65) Prior Publication Data
US 2015/0050231 A1     Feb. 19, 2015

(30) Foreign Application Priority Data

Mar. 30, 2012 (JP) ................................. 2012-079616
Mar. 30, 2012 (JP) ................................. 2012-079954
Mar. 30, 2012 (JP) ................................. 2012-080354

(51) Int. Cl.
| | | |
|---|---|---|
| A61K 8/87 | (2006.01) | |
| A61K 8/86 | (2006.01) | |
| A61Q 5/06 | (2006.01) | |
| A61K 8/81 | (2006.01) | |
| A61K 8/91 | (2006.01) | |
| A61K 8/34 | (2006.01) | |
| A61K 8/41 | (2006.01) | |
| A61K 8/39 | (2006.01) | |

(52) U.S. Cl.
CPC ... *A61K 8/91* (2013.01); *A61K 8/34* (2013.01); *A61K 8/345* (2013.01); *A61K 8/39* (2013.01); *A61K 8/416* (2013.01); *A61K 8/8158* (2013.01); *A61K 8/8164* (2013.01); *A61K 8/8176* (2013.01); *A61K 8/8182* (2013.01); *A61K 8/86* (2013.01); *A61K 8/87* (2013.01); *A61Q 5/06* (2013.01)

(58) Field of Classification Search
CPC ......... A61Q 1/02; A61Q 19/00; A61Q 17/04; A61Q 1/10; A61Q 1/06; A61Q 15/00; A61Q 1/08; A61Q 19/08; A61Q 19/10; A61Q 5/02; A61Q 19/02; A61Q 1/12; A61Q 5/06; A61Q 3/02; A61Q 5/002; A61Q 1/04
See application file for complete search history.

(56) References Cited

FOREIGN PATENT DOCUMENTS

| | | | |
|---|---|---|---|
| JP | 57-54111 | 3/1982 | |
| JP | 2-25411 | 1/1990 | |
| JP | 4-36218 | 6/1992 | |
| JP | 4-359913 | 12/1992 | |
| JP | 04359913 A | * 12/1992 | ............... A61K 8/87 |
| JP | 2704730 | 1/1998 | |
| JP | 10-45546 | 2/1998 | |
| JP | 11-124316 | 5/1999 | |
| JP | 2002-060321 | 2/2002 | |
| JP | 2004-067622 | 3/2004 | |
| JP | 2004-182612 | 7/2004 | |
| JP | 2009-242257 | 10/2009 | |
| JP | 2009-242257 A | * 10/2009 | ............... A61K 8/87 |
| JP | 2009-2422547 A | * 10/2009 | ............... A61K 8/87 |
| JP | 2010-518190 | 5/2010 | |
| JP | 2010-229070 | 10/2010 | |
| WO | 2011/162370 | 12/2011 | |
| WO | 2012/132444 | 10/2012 | |

OTHER PUBLICATIONS

JP2009242257A, Udagawa et al., published Oct. 22, 2009, translation of document.*
JP04359913, Ito et al. published Dec. 14, 1992, translation of abstract.*
JP2009242257A, Udagawa et al., published Oct. 22, 2009, translation of abstract.*
JP2009232257A, Udagawa et al., published Oct. 22, 2009, translation of document.*
JP04359913, Ito et al., published Dec. 14, 1992, translation of abstract.*

* cited by examiner

*Primary Examiner* — Audrea Buckley
(74) *Attorney, Agent, or Firm* — Occhiuti & Rohlicek LLP

(57) ABSTRACT

It is an object of the present invention to provide a hair cosmetic achieving a hair-setting property without causing flaking and further having an excellent hair-rearranging property and non-stickiness. The hair cosmetic of the present invention includes the following components (A) to (D):
  (A) a (meth)acrylic silicone-based graft copolymer;
  (B) at least one film-forming polymer selected from nonionic, amphoteric, and cationic polymers;
  (C) a monohydric lower alcohol; and
  (D) at least one selected from polyalkylene glycols and sugar alcohols, wherein
the component (A) and the component (B) preferably have a content ratio (A):(B) within a mass ratio range of 1:10 to 2:1; and the hair cosmetic preferably has a viscosity at 25° C. of 1000 mPa·s or less.

12 Claims, No Drawings

HAIR COSMETIC

CROSS REFERENCE TO RELATED APPLICATIONS

This application is a U.S. application under 35 USC §371 of International Application No. PCT/JP2013/002127 filed on Mar. 28, 2013, which claims priority to Japanese Application Nos. 2012-079616, 2012-079954 and 2012-080354, all of which were filed on Mar. 30, 2012, the contents of which are hereby incorporated by reference in their entirety.

TECHNICAL FIELD

The present invention relates to a hair cosmetic. More specifically, the invention relates to a hair cosmetic containing a (meth)acrylic silicone-based graft copolymer, a film-forming polymer, a monohydric lower alcohol, and at least one selected from polyalkylene glycols and sugar alcohols. The hair cosmetic has an excellent hairstyling property, hardly causes flaking, is capable of restyling hair, and is low in stickiness.

BACKGROUND ART

In hair cosmetics, film-forming polymers and oily components have been conventionally used as hair-setting agents for fixing and keeping hair styles. For example, as the film-forming polymers, various types of polymers, such as anionic, amphoteric, cationic, and nonionic polymers, have been used alone or in combination depending on the characteristics of products such as hair spray, hair mousse, color lotion, and hair gel. Although such film-forming polymers can impart excellent hair-setting properties to the products, the resulting films are hard, and feelings such as stiffness and squeakiness occur in some cases. In the oily components, although the hair-setting properties are not high compared to those of the film-forming polymers, since no films are formed, the hardness and stiffness are low. In addition, the oily components have effect of providing gloss and have been therefore widely used as useful hair-setting agents in, in particular, emulsifier-type hair cosmetics. In particular, solid oils are excellent in restoring the style of hair out of shape, a hair-rearranging property, and have been widely used in emulsifier-type hair dressings (e.g., see Patent Documents 1 to 3).

Thus, technologies of formulating hair cosmetics excellent not only in the hair-setting property but also in the hair-rearranging property have been actively investigated in recent years. For example, a technology of combining qualitative and quantitative characteristics of film-forming polymers is known (e.g., see Patent Documents 4 and 5).

Furthermore, in addition to the combination of existing components, components that further add values to products have been also developed. For example, since (meth)acrylic polymer is transparent and it forms a film and has good workability, it has been widely used as a coating material, an adhesive material, a material for ink, a material for external use on skin, a cosmetic material, etc. However, since (meth)acrylic polymer has high polarity, it has also had many problems. As such, various copolymers have been developed so far. Examples of the thus developed copolymers include: an acryl-silicone-based graft copolymer obtained by radical copolymerization of a dimethylpolysiloxane compound having a radically polymerizable group at one end of a molecular chain thereof and a radically polymerizable monomer having acrylate and/or methacrylate as a main body (see for example, Patent Document 6); and an amphiphilic block copolymer comprising a polysiloxane block and a cationic block (see for example, Patent Document 7).

PRIOR ART DOCUMENTS

Patent Documents

Patent Document 1: Japanese unexamined Patent Application Publication No. 10-45546
Patent Document 2: Japanese unexamined Patent Application Publication No. 11-124316
Patent Document 3: Japanese unexamined Patent Application Publication No. 2004-67622
Patent Document 4: Japanese unexamined Patent Application Publication No. 2004-182612
Patent Document 5: Japanese unexamined Patent Application Publication No. 2010-229070
Patent Document 6: Japanese Patent No. 2704730
Patent Document 7: Japanese unexamined Patent Application Publication (Translation of PCT Application) No. 2010-518190

SUMMARY OF THE INVENTION

Object to be Solved by the Invention

However, in the use of a film-forming polymer forming a high-strength film for achieving a high hair-setting property, a stiff feeling or occurrence of flaking has been caused in some cases. In contrast, a film-forming polymer forming a low-strength film has a problem of not proving a sufficient hair-setting property. It has been therefore difficult to achieve a hair-setting property without causing flaking.

Furthermore, pharmaceutical agents containing both a film-forming polymer and a sugar alcohol and pharmaceutical agents containing both a film-forming polymer and a polyalkylene glycol are excellent in, for example, hair-rearranging properties, but are insufficient in prevention of flaking derived from the film-forming polymer. In addition, these technologies have been insufficient in impartation of feeling of gloss by hair cosmetics.

Accordingly, it is an object of the present invention to provide a hair cosmetic achieving a hair-setting property without causing flaking and also having an excellent hair-rearranging property and non-stickiness.

Means to Solve the Object

In the light of the circumstances described above, the present inventors have conducted intensive studies directed towards solving the above-mentioned object and, as a result, have found that a hair cosmetic achieving non-flaking and non-stickiness, while maintaining a satisfactory hair-setting property and a hair-rearranging property, can be obtained by adding a (meth)acrylic silicone-based graft copolymer to a conventional hair dressing containing at least one film-forming polymer selected from nonionic, amphoteric, and cationic polymers and at least one selected from sugar alcohols and polyalkylene glycols, and have accomplished the present invention.

That is, the present invention relates to:
(1) A hair cosmetic comprising the following components (A) to (D):
(A) a (meth)acrylic silicone-based graft copolymer;
(B) at least one film-forming polymer selected from nonionic, amphoteric, and cationic polymers;

(C) a monohydric lower alcohol; and (D) at least one selected from polyalkylene glycols and sugar alcohols;

(2) The hair cosmetic according to (1) above, wherein the component (A) is a (meth)acrylic silicone-based graft copolymer that is obtained by reacting the following radically polymerizable monomers (a), (b), (c), and (d) and is dissolved at a level of 50 mass % or more in 99.5% ethanol at 25° C.:

(a) a compound represented by the following general formula (I):

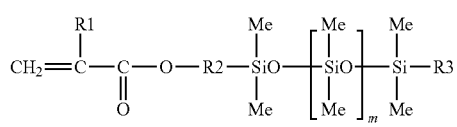

(wherein Me represents a methyl group, R1 represents a hydrogen atom or a methyl group, R2 represents a linear or branched divalent saturated hydrocarbon group containing 1 to 10 carbon atoms, which optionally comprises one or two ether bonds, R3 represents a saturated hydrocarbon group containing 1 to 10 carbon atoms, and m represents any of integer of 5 to 100);

(b) at least one selected from a compound represented by the following general formula (II):

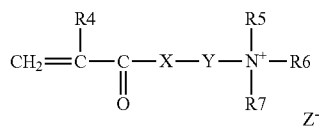

(wherein R4 represents a hydrogen atom or a methyl group, R5, R6 and R7, which are the same or different, each represent a hydrogen atom or an alkyl group containing 1 to 4 carbon atoms, X represents —O—, —NH—, —O—CH$_2$— or —O—CH$_2$CH(OH)—, Y represents a linear or branched divalent saturated hydrocarbon group containing 1 to 4 carbon atoms, and Z$^-$ represents a counter anion), and a compound represented by the following formula (III):

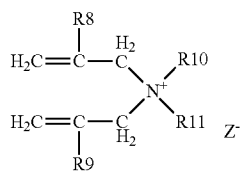

(wherein R8 and R9, which are the same or different, each represent a hydrogen atom or an alkyl group containing 1 to 4 carbon atoms, R10 and R11, which are the same or different, each represent a hydrogen atom or an alkyl group containing 1 to 18 carbon atoms, and Z$^-$ represents a counter anion);

(c) a compound represented by the following general formula (IV):

(wherein R12 represents a hydrogen atom or a methyl group, and R13 represents a hydrogen atom or a linear or branched alkyl group containing 1 to 3 carbon atoms); and (d) a compound represented by the following general formula (V):

(wherein R14 represents a hydrogen atom or a methyl group, and R15 represents a hydroxyalkyl group containing 1 to 4 carbon atoms);

(3) The hair cosmetic according to (1) above, wherein the component (B) is at least one selected from a polyvinyl pyrrolidone, a vinyl pyrrolidone/vinyl acetate copolymer, and a hydroxypropyl acrylate/butylaminoethyl methacrylate/octylamide acrylate copolymer;

(4) The hair cosmetic according to (2) above, wherein the component (B) is at least one selected from a polyvinyl pyrrolidone, a vinyl pyrrolidone/vinyl acetate copolymer, and a hydroxypropyl acrylate/butylaminoethyl methacrylate/octylamide acrylate copolymer;

(5) The hair cosmetic according to any one of (1) to (4) above, wherein the component (A) and the component (B) have a content ratio (A):(B) within a mass ratio range of 1:10 to 2:1;

(6) The hair cosmetic according to any one of (1) to (4) above, having a viscosity at 25° C. of 1000 mPa·s or less;

(7) The hair cosmetic according to (5) above, having a viscosity at 25° C. of 1000 mPa·s or less; and (8) The hair cosmetic according to (1) above, being contained in a container available for spraying the hair cosmetic as mist.

Effect of the Invention

The hair cosmetic of the present invention advantageously achieves a satisfactory hair-setting property without causing flaking, has a high hair-rearranging property, and further has less stickiness.

Furthermore, the hair cosmetic of the present invention is also excellent in a fluffy feeling, when it contains both a polyalkylene glycol and a sugar alcohol.

MODE OF CARRYING OUT THE INVENTION

The present invention will now be specifically described, in particular, on the basis of preferred embodiments thereof. Throughout the specification, a numerical range defined with "to" is meant to include the numbers preceding and following the "to".

(1) Component (A) Contained in Hair Cosmetic of the Present Invention

The term "(meth)acrylic silicone-based graft copolymer" at least encompasses not only polymers obtained by reacting the following radically polymerizable monomers (a), (b), (c), and (d) but also polymers obtained by reacting another copolymerizable monomer in addition to the monomers (a) to (d).

The term "(meth)acryl" is used in the present invention to include acryl and methacryl.

The (meth)acrylic silicone-based graft copolymer of the present invention is dissolved at a level of 50 mass % or more in 99.5% ethanol at 25° C.

The ratio of individual monomers used is not particularly limited, as long as it provides the effect of the present invention. It is preferable that (a)=20 to 50 mass %, (b)=0.5 to 4 mass %, (c) and (d)=46 to 79.5 mass %, and (c)/(d)=0.5 to 1.5, based on the total mass of the monomers (a) to (d).

When copolymerizable monomers other than the monomers (a) to (d) are used, the monomers (a) to (d) are preferably used at a level of 66.5 mass % or more in total based on the total mass.

It is to be noted that the term "ratio of monomers used" has roughly the same definitions as "the composition ratio of monomers in a copolymer."

The viscosity (unit: mPa·s=CS) of the (meth)acrylic silicone-based graft copolymer of the present invention that has been dissolved at a level of 20 mass % in 99.5% ethanol, which is measured using a B type rotation viscometer at 25° C., is 50 to 250, and preferably 70 to 150.

In addition, the Tg of the (meth)acrylic silicone-based graft copolymer of the present invention is preferably −10° C. to 40° C., and more preferably 0° C. to 30° C.

Herein, Tg indicates the Tg value calculated by the following Fox formula:

$$1/Tg = W_1/Tg_1 + W_2/Tg_2 + \ldots + W_n/Tg_n$$

In the above formula, $W_1$ to $W_n$ each indicate the weight fraction of each of an n type of monomers used in the synthesis of a base for hair cosmetics. $Tg_1$ to $Tg_n$ each represent the glass transition temperature of a homopolymer obtained by polymerization of each monomer alone.

Moreover, the (meth)acrylic silicone-based graft copolymer of the present invention includes various forms such as a random copolymer and a block copolymer.

Hereinafter, monomers used as raw materials for a copolymer will be described.

(a) Radically polymerizable monomer represented by the following general formula (I)

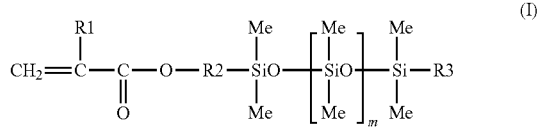

In the general formula (I), Me represents a methyl group, and R1 represents a hydrogen atom or a methyl group.

In addition, R2 represents a linear or branched divalent saturated hydrocarbon group containing 1 to 10 carbon atoms, which optionally comprises one or two ether bonds. Specific examples of such a linear or branched divalent saturated hydrocarbon group include —CH$_2$—, —(CH$_2$)$_2$—, —(CH$_2$)$_5$—, —(CH$_2$)$_{10}$—, —CH$_2$—CH(CH$_3$)—CH$_2$—, —CH$_2$CH$_2$OCH$_2$CH$_2$CH$_2$—, CH$_2$CH$_2$OCH(CH$_3$)CH$_2$—, and —CH$_2$CH$_2$OCH$_2$CH$_2$CH$_2$OCH$_2$CH$_2$—.

R3 represents a saturated hydrocarbon group containing 1 to 10 carbon atoms. Specific examples of such a saturated hydrocarbon group include: alkyl groups containing 1 to 10 carbon atoms, such as a methyl group, an ethyl group, a n-propyl group, an i-propyl group, a n-butyl group, a s-butyl group, an i-butyl group, a t-butyl group, a n-pentyl group, a n-hexyl group, a n-nonyl group, an isononyl group, and a n-decyl group; cycloalkyl groups containing 3 to 10 carbon atoms, such as a cyclopropyl group, a cyclobutyl group, a cyclopentyl group, a cyclohexyl group, a cycloheptyl group, a cyclooctyl group, and a cyclododecyl group; and cycloalkylalkyl groups containing 4 to 10 carbon atoms, such as a cyclopropylmethyl group, a 2-cyclopropylethyl group, a cyclobutylmethyl group, a cyclopentylmethyl group, a 3-cyclopentylpropyl group, a cyclohexylmethyl group, a 2-cyclohexylethyl group, a cycloheptylmethyl group, and a cyclooctylmethyl group.

Also, in the formula, m represents any of integer of 5 to 100.

The monomer represented by the formula (I) can be obtained, for example, by subjecting a (meth)acrylate-substituted chlorosilane compound represented by the following formula (I-a):

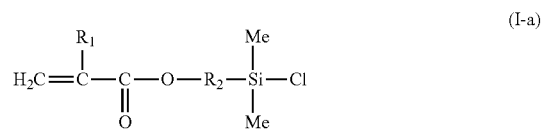

and polysiloxane comprising a substitution of a hydroxyl group at one end, represented by the following formula (I-b):

to a dehydrochlorination reaction according to an ordinary method. However, the synthetic method is not limited thereto.

Specific examples of the monomer represented by the formula (I) are as follows. It is to be noted that, in the following formulae, Me represents a methyl group and n-Bu represents a n-butyl group.

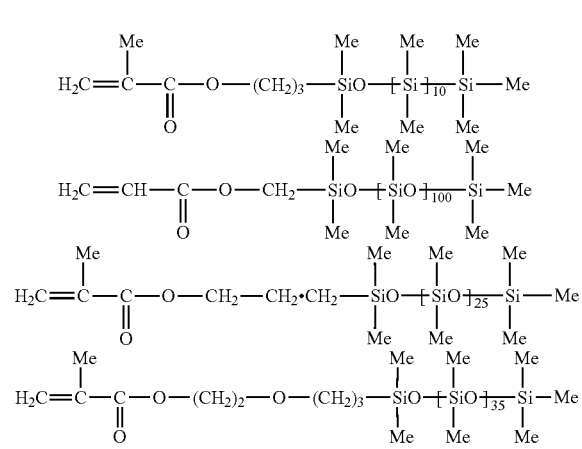

-continued

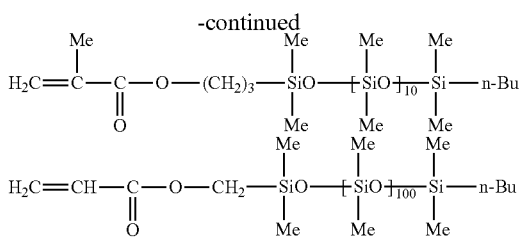

(b) Radically polymerizable monomer represented by the following formula (II) or formula (III)

Component (b) is at least one selected from cationic compounds represented by the following formula (II) and formula (III):

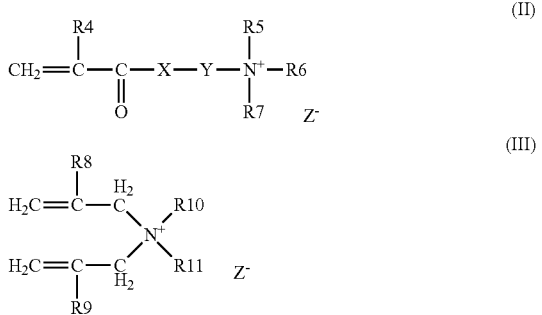

In the above formula (II), R4 represents a hydrogen atom or a methyl group.

R5, R6 and R7, which are the same or different, each represent a hydrogen atom or an alkyl group containing 1 to 4 carbon atoms. Examples of the alkyl group containing 1 to 4 carbon atoms include a methyl group, an ethyl group, a n-propyl group, an i-propyl group, a n-butyl group, a s-butyl group, an i-butyl group, and a t-butyl group.

X represents —O—, —NH—, —O—CH$_2$— or —O—CH$_2$CH(OH)—.

Y represents a linear or branched divalent saturated hydrocarbon group containing 1 to 4 carbon atoms. Examples of the linear or branched divalent saturated hydrocarbon group containing 1 to 4 carbon atoms include —CH$_2$—, —(CH$_2$)$_2$—, —(CH$_2$)$_3$—, —(CH$_2$)$_4$—, and —CH$_2$—CH(CH$_3$)—CH$_2$—.

Z$^-$ represents a counter anion. Examples of the counter anion include a chlorine ion, a bromine ion, a hydrogen sulfate ion, a nitric acid ion, a perchloric acid ion, a boron tetrafluoride ion, and a phosphorus hexafluoride ion.

In the above formula (III), R8 and R9, which are the same or different, each represent a hydrogen atom or an alkyl group containing 1 to 4 carbon atoms. Examples of the alkyl group containing 1 to 4 carbon atoms include a methyl group, an ethyl group, a n-propyl group, an i-propyl group, a n-butyl group, a s-butyl group, an i-butyl group, and a t-butyl group.

R10 and R11, which are the same or different, each represent a hydrogen atom or an alkyl group containing 1 to 18 carbon atoms. Examples of the alkyl group containing 1 to 18 carbon atoms include a methyl group, an ethyl group, a n-propyl group, an i-propyl group, a n-butyl group, a s-butyl group, an i-butyl group, a t-butyl group, a n-pentyl group, a n-hexyl group, a n-nonyl group, an isononyl group, a n-decyl group, a lauryl group, a tridecyl group, a myristyl group, a n-pentadecyl group, a palmityl group, a heptadecyl group, and a stearyl group.

(c) Radically polymerizable monomer represented by the following formula (IV)

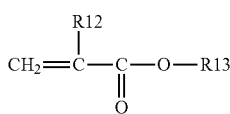

In the above formula, R12 represents a hydrogen atom or a methyl group.

R13 represents a hydrogen atom or a linear or branched alkyl group containing 1 to 3 carbon atoms. Examples of the linear or branched alkyl group containing 1 to 3 carbon atoms include a methyl group, an ethyl group, a n-propyl group, and an i-propyl group.

(d) Radically polymerizable monomer represented by the following formula (V)

In the above formula, R14 represents a hydrogen atom or a methyl group.

R15 represents a hydroxyalkyl group containing 1 to carbon atoms. Examples of the hydroxyalkyl group containing 1 to 4 carbon atoms include a hydroxymethyl group, a 2-hydroxyethyl group, a 3-hydroxy-n-propyl group, and a 4-hydroxy-n-butyl group.

(e) Other Copolymerizable Monomers

Other copolymerizable monomers include the following compounds.

((Meth)Acrylic Monomers)

(Meth)acrylic esters having a linear, branched or alicyclic hydrocarbon group such as n-butyl(meth)acrylate, isobutyl (meth)acrylate, t-butyl(meth)acrylate, 2-ethylhexyl(meth) acrylate, n-hexyl(meth)acrylate, n-octyl(meth)acrylate, cyclohexyl(meth)acrylate, decyl(meth)acrylate, undecyl (meth)acrylate, lauryl(meth)acrylate, tridecyl(meth)acrylate, myristyl(meth)acrylate, pentadecyl(meth)acrylate, palmityl (meth)acrylate, heptadecyl(meth)acrylate, stearyl(meth) acrylate, isostearyl(meth)acrylate, oleyl(meth)acrylate and behenyl(meth)acrylate; acrylonitrile; (meth)acrylamides such as acrylamide, diacetone acrylamide, N,N-dimethylacrylamide, N-t-butylacrylamide, N-octylacrylamide and N-t-octylacrylamide; (meth)acrylamides containing a sulfonic acid group such as 2-(meth)acrylamide-2-methylpropanesulfonic acid; alkylaminoalkyl(meth)acrylates such as aminoethyl(meth)acrylate, t-butylaminoethyl methacrylate and methylaminoethyl(meth)acrylate; dialkylaminoalkyl (meth)acrylates such as dimethylaminoethyl(meth)acrylate and diethylaminoethyl(meth)acrylate; dialkylaminoalkyl (meth)acrylamides such as dimethylaminoethyl(meth)acrylamide and diethylaminoethyl(meth)acrylamide; esters of cyclic compounds with (meth)acrylic acids, such as tetrahydrofurfuryl(meth)acrylate, isobornyl(meth)acrylate and glycidyl(meth)acrylate; (meth)acrylic acid alkoxy alkyl esters such as ethoxyethyl(meth)acrylate and methoxyethyl(meth) acrylate; monoesters of polyalkylene glycols with (meth) acrylic acids, such as polyethylene glycol mono(meth)acrylate and polypropylene glycol mono(meth)acrylate; (meth)

acryl esters containing a sulfonic acid group; methacryloyloxy alkyl phosphate monoesters such as (meth)acryloyloxy ethyl phosphate; glyceryl(meth)acrylate, 2-methacryloyloxyethylsuccinic acid, 2-(meth)acryloyloxyethylphthalic acid, β-carboxyethyl acrylate, acryloyloxyethyl succinate, 2-(meth)acryloyloxyethyltetrahydrophthalic acid and 2-(meth)acryloyloxyethylhexahydrophthalic acid; and (meth)acrylates having two or more ethylenically unsaturated double bonds, such as 1,4-butanediol di(meth)acrylate, 1,6-hexanediol di(meth)acrylate, ethylene glycol di(meth)acrylate, polyethylene (n=2 to 50) glycol di(meth)acrylate, propylene glycol di(meth)acrylate, polypropylene (n=2 to 50) glycol di(meth)acrylate, butylene glycol di(meth)acrylate, dipentyl glycol di(meth)acrylate, neopentyl glycol di(meth)acrylate, trimethylolpropane di(meth)acrylate, methylenebis acrylamide, bisphenol F EO-modified (n=2 to 50) di(meth)acrylate, bisphenol A EO-modified (n=2 to 50) diacrylate, bisphenol S EO-modified (n=2 to 50) di(meth)acrylate, trimethylolethane tri(meth)acrylate, trimethylolpropane tri(meth)acrylate, trimethylolpropane tricaprolactonate tri(meth)acrylate, trimethylolhexane tri(meth)acrylate, pentaerythritol tri(meth)acrylate, pentaerythritol tetra(meth)acrylate, diglycerine tetra(meth)acrylate, ditrimethylolpropane tetra(meth)acrylate, ditrimethylolpropane tetracaprolactonate, tetra(meth)acrylate, ditrimethylolethane tetra(meth)acrylate, ditrimethylolbutane tetra(meth)acrylate, ditrimethylolhexane tetra(meth)acrylate, dipentaerythritol penta(meth)acrylate, dipentaerythritol hexa(meth)acrylate, tripentaerythritol hexa(meth)acrylate, tripentaerythritol hepta(meth)acrylate and tripentaerythritol octa(meth)acrylate.

(Monomers Other than (Meth)Acrylic Monomers)

Unsaturated monocarboxylic acids such as crotonic acid;
aromatic vinyl compounds such as styrene;
unsaturated dicarboxylic acids such as itaconic acid, maleic acid, fumaric acid, maleic anhydride and citraconic acid;
monoalkyl esters of unsaturated dicarboxylic acids, such as maleic acid monoalkyl ester, fumaric acid monoalkyl ester and itaconic acid monoalkyl ester;
alkene sulfonic acids such as vinylsulfonic acid and (meth)allylsulfonic acid;
aromatic vinyl group-containing sulfonic acids such as α-methylstyrenesulfonic acid;
primary to tertiary amino group-containing unsaturated compounds such as (meth)allylamine;
amino group-containing aromatic vinyl compounds such as N,N-dimethylaminostyrene;
compounds having two or more ethylenically unsaturated double bonds, such as divinylbenzene, diisopropenylbenzene and trivinylbenzene;
urethane oligomers having two or more ethylenically unsaturated double bonds;
silicone compounds having two or more ethylenically unsaturated double bonds;
and vinyl acetate and vinyl pyrrolidone.

The amount of component (A) contained in the hair cosmetic of the present invention is not particularly limited, and is preferably 0.01 to 10 mass % (hereinafter, abbreviated to simply "%"), more preferably 0.05% to 6%, based on the total mass of the composition. This range is suitable for achieving the effects of not causing flaking and stickiness.

(Production Method)

The (meth)acrylic silicone-based graft copolymer can be produced by copolymerizing the radically polymerizable monomers (a) to (d) and as necessary another copolymerizable (meth)acrylic monomer by a known method. For example, copolymerization can be carried out in the presence of a common radical polymerization initiator such as benzoyl peroxide, lauroyl peroxide, and azobisisobutyronitrile. Any of a solution polymerization method, an emulsification polymerization method, a suspension polymerization method, and a bulk polymerization method can be applied herein. Among these methods, the solution polymerization method is preferable because it can easily adjust the molecular weight of the obtained graft copolymer to the optimal range. Examples of a solvent used herein include: aromatic hydrocarbons such as benzene, toluene or xylene; ketones such as methyl ethyl ketone or methyl isobutyl ketone; esters such as ethyl acetate or isobutyl acetate; and alcohols such as isopropanol or butanol. The solvent may be used singly or in the form of a mixture consisting of two or more types as described above.

The polymerization reaction can be carried out in a temperature range from 50° C. to 180° C., and preferably from 60° C. to 120° C. The reaction can be terminated for approximately 5 to 10 hours under the above-mentioned conditions.

(2) Component (B) Contained in Hair Cosmetic of the Present Invention

The nonionic, amphoteric, or cationic film-forming polymer contributes to the hair-setting property and is not particularly limited as long as it is any polymer that is usually contained in hair cosmetics. Examples thereof include the following polymers.

Examples of the nonionic polymer include polyvinyl pyrrolidones, vinyl pyrrolidone/vinyl acetate copolymers, polyvinyl alcohols, and polyurethanes, and a commercially available product, such as Luviskol K (manufactured by BASF), PVP/VA (manufactured by ISP), Gohsenol series (manufactured by The Nippon Synthetic Chemical Industry Co., Ltd.), Kuraray Poval series (manufactured by Kuraray Co., Ltd.), and Acorn series (manufactured by Osaka Organic Chemical Industry Ltd.), can be used.

Examples of the amphoteric polymer include N-methacryloyl ethyl N,N-dimethylammonium/α-N-methylcarboxybetaine/alkyl methacrylate copolymers, hydroxypropyl acrylate/butylaminoethyl methacrylate/octylamide acrylate copolymers, acrylic acid/dimethyldiallylammonium chloride/acrylamide copolymers, and dimethyldiallylammonium chloride/acrylic acid copolymers, and a commercially available product, such as Yukaformer series (manufactured by Mitsubishi Chemical Corporation), Amphomer series (manufactured by National Starch and Chemical Company), and Merquat 3330 and Merquat 280 (manufactured by Calgon Corporation), can be used.

Examples of the cationic polymer include vinyl pyrrolidone/N,N-dimethylaminoethyl methacrylate copolymer diethyl sulfate salts, diallyldimethylammonium chloride/hydroxyethyl cellulose, glycidyltrimethylammonium chloride/hydroxyethyl cellulose, dimethyldiallylammonium chloride polymers, and dimethyldiallylammonium chloride/acrylamide copolymers, and a commercially available product, such as Gafquat series 734 and 755 (manufactured by ISP), Catinal series (manufactured by Toho Chemical Industry Co., Ltd.), Celquat series (manufactured by National Starch and Chemical Company), Merquat series 100 and 550 (manufactured by Calgon Corporation), H. C. Polymer (manufactured by Osaka Organic Chemical Industry Ltd.), and Catinal series (manufactured by Toho Chemical Industry Co., Ltd.), can be used.

The nonionic, amphoteric, and cationic polymers to be used as the at least one film-forming polymer can be used singly or in combinations of two or more. Among these polymers, polyvinyl pyrrolidones, vinyl pyrrolidone/vinyl acetate copolymers, and hydroxypropyl acrylate/butylaminoethyl methacrylate/octylamide acrylate copolymers are suitable for exhibiting a hair-setting property.

The amount of the at least one film-forming polymer selected from nonionic, amphoteric, and cationic polymers is not particularly limited, and is preferably 0.1 to 30 mass % and more preferably 1 to 20 mass %. Furthermore, an amount range of 1 to 15 mass % is suitable for achieving non-flaking.

The amount of the at least one film-forming polymer selected from nonionic, amphoteric, and cationic polymers is not particularly limited, and a content ratio (A):(B) of the component (A) and the component (B) within a mass ratio range of 1:10 to 2:1 is suitable for achieving a hair-setting property without causing flaking.

(3) Component (C) Contained in Hair Cosmetic of the Present Invention

The monohydric lower alcohol is used as a solvent for the component (A) and is not particularly limited as long as it is any monohydric lower alcohol that is usually contained in hair cosmetics, and examples thereof include ethanol and isopropanol. In particular, ethanol is preferred.

The amount of the monohydric lower alcohol used in the present invention is not particularly limited, and can be within a range of approximately 10 to 99 mass %. The component (C) may be composed of one or more monohydric lower alcohols.

(4) Component (D) Contained in Hair Cosmetic of the Present Invention

In the present invention, the component (D) is at least one selected from the polyalkylene glycols (D1) and sugar alcohols (D2) mentioned above. The polyalkylene glycols and the sugar alcohols may be each used singly or in combinations of two or more.

The polyalkylene glycol is contained for achieving a hair-rearranging property, and examples thereof include polypropylene glycols in which propylene oxide structural units are polymerized, polyethylene glycols in which ethylene oxide structural units are polymerized, polybutylene glycols in which butylene oxide structural units are polymerized, and copolymers thereof. The number of carbon atoms in an alkylene unit of the polyalkylene glycol is not particularly limited and is usually 2 to 6.

The polyalkylene glycol may be liquid, solid, or a mixture thereof at 25° C.

The polyalkylene glycol used in the present invention may be a commercially available one, and examples thereof include PEG 200, PEG 300, PEG 400, PEG 600, PEG 1000, PEG 1500, PEG 2000, PEG 4000, PEG 6000, PEG 11000, and PEG 20000 (manufactured by NOF Corporation, Toho Chemical Industry Co., Ltd., or Sanyo Chemical Industries, Ltd.), and Uniol D-1000 and Uniol D-2000 (manufactured by NOF Corporation).

The number-average molecular weight of the polyalkylene glycol used in the present invention is not particularly limited and is preferably 200 to 20000.

When the polyalkylene glycol is used alone, the number-average molecular weight is preferably 400 to 20000. When the polyalkylene glycol is used together with the sugar alcohol, the number-average molecular weight is preferably 200 to 1000 and more preferably 300 to 600.

The number-average molecular weight is measured by end-group analysis based on the average molecular weight test described in the Japanese Standards of Quasi-drug Ingredients, and specifically measured on the basis of the hydroxyl value determined by titration.

The sugar alcohol mainly contributes to, for example, the hair-rearranging property and is not particularly limited as long as it is any sugar alcohol that is usually used in cosmetics and may be derived from any substance and may be produced from by any method. Examples of the sugar alcohol include sorbitol, erythritol, maltitol, xylitol, ribitol, arabitol, galactitol, inositol, mannitol, pentaerythritol, and reduced palatinose. More preferred sugar alcohols are sorbitol and maltitol from the viewpoint of the hair-rearranging property. The sugar alcohol used in the present invention is not particularly limited and may be a commercially available one, such as sorbitol S (manufactured by Nikken Chemical and Synthetic Industry Co., Ltd.) and Amalty syrup (Mabit) (manufactured by Mitsubishi Shoji Foodtech Co., Ltd.).

The amount of component (D) is preferably 0.1 to 20 mass %, more preferably 2 to 10 mass %, based on the total mass of the hair cosmetic.

In the present invention, a combination of the polyalkylene glycol (D1) and the sugar alcohol (D2) at a specific mass ratio can further enhance the effect of inhibiting flaking and stickiness of the polyalkylene glycol and the effect of hair-setting by the sugar alcohol. A content ratio D1/D2 (unit:mass) within a range of 0.25 to 4, preferably 0.5 to 2, is particularly suitable not only for excellent non-flaking and a hair-rearranging property but also for an effect of imparting feeling of gloss to hair.

(5) Other Components of Hair Cosmetic of the Present Invention

The hair cosmetic of the present invention can contain, in addition to the components described above, components that are usually contained in pharmaceutical agents, such as cosmetics and quasi-drugs, in qualitative and quantitative ranges that do not impair the effects of the present invention. Examples of the optional components include water (e.g., purified water, hot spring water, and deep water), surfactants, oil agents, gelling agents, powders, polyhydric alcohols, antimicrobial agents, antiseptics, pH adjusters, refrigerants, vitamins, beauty ingredients, fragrances, deodorants, salts, chelating agents, UV absorbers, and plant extracts.

Examples of the surfactant include cationic, anionic, nonionic, and amphoteric surfactants.

Examples of the cationic surfactant include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, di stearyldimethylammonium chloride, dicocoyldimethylammonium chloride, dioctyldimethylammonium chloride, di(POE)oleylmethylammonium (2E.O.) chloride, benzalkonium chloride, stearyldimethylbenzylammonium chloride, lanolin-derived quaternary ammonium salts, stearic diethylaminoethylamide, stearic dimethylaminopropylamide, behenamidopropyldimethylhydroxypropylammonium chloride, stearoylcolaminoformylmethylpyridinium chloride, cetylpyridinium chloride, tall oil alkylbenzyl hydroxyethyl imidazolinium chloride, and dicocoylethyl hydroxyethylmonium methosulfate.

Examples of the anionic surfactant include fatty acid soaps such as sodium stearate and triethanolamine palmitate;

alkyl ether carboxylates, alkyl sulfonates, alkene sulfonates, fatty acid ester sulfonates, fatty acid amide sulfonates, alkyl sulfonates and sulfonates of formalin condensates of the alkyl sulfonates, alkyl sulfuric acid ester salts, secondary higher alcohol sulfuric acid ester salts, alkyl and allyl ether sulfuric acid ester salts, sulfuric acid ester salts of fatty acid esters, sulfuric acid ester salts of fatty acid alkylolamides, and sulfuric acid ester salts of, for example, turkey-red oils; and alkyl phosphates, alkyl ether phosphates, alkyl allyl ether phosphates, amidophosphates, N-acylamino acid salts, acyl isethionate, N-acylalkyltaurine salts, and N-acyl polypeptide salts.

Examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkylphenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oil fatty acid ester, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene/alkyl co-modified organopolysiloxane, alkanolamide, sugar ether, and sugar amide.

Examples of the amphoteric surfactants include acetic acid betaines such as octyldimethylaminoacetic acid betaine, lauryldimethylaminoacetic acid betaine, coconut oil fatty acid alkyldimethylaminoacetic acid betaine, coconut oil fatty acid amide propyldimethylaminoacetic acid betaine, and lauric acid amide propyldimethylaminoacetic acid betaine; sulfobetaines such as laurylsulfobetaine;

imidazoline derivatives such as N-coconut oil fatty acid acyl-N-carboxymethyl-N-hydroxyethyl ethylenediamine sodium and N-coconut oil fatty acid acyl-N-carboxymethoxyethyl-N-carboxymethyl ethylenediamine disodium; and aminocarboxylates such as coconut oil alkyliminodicarboxylates.

These surfactants can be appropriately selected and can be used singly or in combinations of two or more.

Examples of the oil agent that can be used herein include oily components such as higher alcohol, hydrocarbon oil, ester oil, oils and fats, and silicone. Specific examples include: higher alcohols such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, sitosterol, lanosterol, and monostearyl glycerin ether (batyl alcohol);

hydrocarbons such as ozokerite, squalane, squalene, ceresin, paraffin, paraffin wax, liquid paraffin, pristine, polyisobutylene, microcrystalline wax, and Vaseline;

ester oils such as diisobutyl adipate, 2-hexyldecyl adipate, di-2-heptylundecyl adipate, monoisostearic acid N-alkyl glycol, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, and diisostearyl malate;

waxes such as beeswax, carnauba wax, candelilla wax, and spermaceti;

vegetable fats and oils such as palm oil, palm kernel oil, olive oil, safflower oil, soybean oil, and cottonseed oil;

animal oils such as tallow, neat's foot oil, beef bone fat, hardened tallow, hardened oil, turtle oil, lard, horse fat, mink oil, cod liver oil, and egg-yolk oil;

lanolin derivatives such as lanolin, liquid lanolin, reduced lanolin, lanolin alcohol, hard lanolin, lanolin acetate, and lanolin fatty acid isopropyl; and silicone such as low polymerized dimethylpolysiloxane, high polymerized dimethylpolysiloxane, methylphenyl polysiloxane, decamethylcyclopentasiloxane, octamethylcyclotetrasiloxane, polyether-modified polysiloxane, a polyoxyalkylene/alkylmethylpolysiloxane/methylpolysiloxane copolymer, alkoxy-modified polysiloxane, alkyl-modified polysiloxane, crosslinked organopolysiloxane, fluorine-modified polysiloxane, amino-modified polysiloxane, glycerin-modified polysiloxane, higher alkoxy-modified silicone, higher fatty acid-modified silicone, silicone resin, silicone rubber, and silicone resin.

Examples of the gelling agent include: amino acid derivatives such as N-lauroyl-L-glutamate, and $\alpha,\gamma$-di-n-butylamine;

dextrin fatty acid esters such as dextrin palmitic acid ester, dextrin stearic acid ester, and dextrin 2-ethylhexanoic acid palmitic acid ester;

sucrose fatty acid esters such as sucrose palmitic acid ester, and sucrose stearic acid ester;

benzylidene derivatives of sorbitol, such as monobenzylidene sorbitol and dibenzylidene sorbitol; and organic-modified clay minerals such as dimethylbenzyldodecyl ammonium montmorillonite clay and dimethyldioctadecyl ammonium montmorillonite clay.

The shape (spherical, acicular, platy, etc.), particle diameter (fumy, fine particle, pigment, etc.), and particle structure (porous, nonporous, etc.) of powders are not limited, as long as the powders may be used for common cosmetics. All types of powders can be used herein.

Examples of the powders used herein include: inorganic powders such as magnesium oxide, barium sulfate, calcium sulfate, magnesium sulfate, calcium carbonate, magnesium carbonate, talc, synthetic mica, mica, kaoline, sericite, muscovite, synthetic mica, phlogopite, lepidolite, biotite, Lithia mica, silicic acid, silicic acid anhydride, aluminum silicate, magnesium silicate, aluminum magnesium silinate, calcium silicate, barium silicate, strontium silicate, tungsten metal salt, hydroxyapatite, vermiculite, HIGILITE, montmorillonite, zeolite, ceramics powder, calcium secondary phosphate, alumina, aluminum hydroxide, boron nitride, and boron nitride.

Examples of the powders used herein include: organic powders such as polyamide powder, polyester powder, polyethylene powder, polypropylene powder, polystyrene powder, polyurethane powder, benzoguanamine powder, polymethylbenzoguanamine powder, tetrafluoroethylene powder, polymethyl methacrylate powder, cellulose powder, silk powder, nylon powder, nylon 12 powder, nylon 6 powder, styrene/acrylic acid copolymer powder, divinylbenzene/styrene copolymer powder, vinyl resin powder, urea resin powder, phenol resin powder, fluorocarbon resin powder, silicon resin powder, acrylic resin powder, melamine resin powder, epoxy resin powder, polycarbonate resin powder, microcrystalline fiber powder, and lauroyl lysine.

Examples of colored pigments include: inorganic red pigments such as iron oxide, iron hydroxide and iron titanate; inorganic brown pigments such as γ-iron oxide;

inorganic yellow pigments such as yellow iron oxide and loess;

inorganic black pigments such as black iron oxide and carbon black;

inorganic violet pigments such as manganese violet and cobalt violet;

inorganic green pigments such as chromium hydroxide, chromium oxide, cobalt oxide and cobalt titanate;

inorganic blue pigments such as iron blue and ultramarine blue;

laked tar pigments, laked natural pigments, and composite powder formed by conjugation of these powders.

Examples of pearl pigments include titanium oxide-coated mica, titanium oxide-coated mica, bismuth oxychloride, titanium oxide-coated bismuth oxychloride, titanium oxide-coated talc, argentine, and titanium oxide-coated colored isinglass.

Examples of metallic powder pigments include aluminum powder, copper powder, and stainless steel powder.

Examples of tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207.

Examples of natural pigments include carmic acid, laccaic acid, carthamin, brazilin and crocin.

These powders may be conjugated with one another, or the surface of which may be treated with an oil agent, silicone, or a fluorine compound.

Examples of the polyhydric alcohols include, in addition to the above-mentioned polyalkylene glycols having a number-average molecular weight of 200 to 20000, glycerin, diglycerin, ethylene glycol, diethylene glycol, triethylene glycol, propylene glycol, dipropylene glycol, 1,3-butylene glycol, polyalkylene glycols having a number-average molecular weight of less than 200, and polyalkylene glycols having a number-average molecular weight of higher than 20000.

Examples of the antimicrobial agent include benzoic acid, sodium benzoate, salicylic acid, carbolic acid, sorbic acid, potassium sorbate, p-chlorometacresol, hexachlorophene, benzalkonium chloride, chlorhexidine, trichlorocarbanilide, photosensitizing dye, bis(2-pyridylthio-1-oxide) zinc, and isopropylmethyl phenol.

Examples of the antiseptics include paraoxybenzoic acid esters and phenoxyethanol.

Examples of the pH adjuster include lactic acid, citric acid, glycolic acid, succinic acid, tartaric acid, malic acid, potassium carbonate, sodium bicarbonate, ammonium bicarbonate, sodium hydroxide, potassium hydroxide, triethanolamine, and monoethanolamine.

Examples of the vitamins include: vitamin A and a derivative thereof; vitamin B and a derivative thereof; vitamin C and a derivative thereof; vitamin E and a derivative thereof; vitamins F such as linolenic acid and a derivative thereof; vitamins K such as phytonadione, menaquinone, menadione, and menadiol; vitamins P such as eriocitrin and hesperidin; and biotin, carnitine, and ferulic acid.

Examples of the refrigerants include L-menthol, camphor, menthyl pyrrolidone carboxylate, and menthyl lactate.

Examples of the beauty ingredients include amino acids, amino acid derivatives, peptides, sterols, homopolymers of 2-methacryloyloxyethyl phospholylcholine, and copolymers of 2-methacryloyloxyethyl phospholylcholine and hydrophobic monomers.

Specifically, examples of the amino acids include glycine, alanine, valine, isoleucine, serine, threonine, aspartic acid, glutamic acid, acetyl glutamic acid, asparagine, glutamine, lysine, hydroxylysine, arginine, cystine, cysteine, acetyl cysteine, methionine, phenylalanine, tyrosine, proline, hydroxyproline, ornithine, citrulline, theanine, and trimethylglycine.

Examples of amino acid derivatives include di(phytosteryl/2-octyldodecyl)N-lauroyl-L-glutamate, di(cholesteryl/behenyl/octyldodecyl)N-lauroyl-L-glutamate, di(cholesteryl/octyldodecyl)N-lauroyl-L-glutamate, di(phytosteryl/behenyl/2-octyldodecyl)N-lauroyl-sarcosine isopropyl, and dioctyldodecyl N-lauroyl-L-glutamate.

The peptides may be derived from any of animals, fish, shell, plants and silk. Specific examples of such peptides include collagen and a derivative thereof or a hydrolysate thereof, elastin and a derivative thereof or a hydrolysate thereof, keratin and a derivative thereof or a hydrolysate thereof, a wheat protein and a derivative thereof or a hydrolysate thereof, and a soybean protein and a derivative thereof or a hydrolysate thereof.

Examples of the sterols include cholesterol and phytosterol.

(6) Method for Producing Hair Cosmetic of the Present Invention

The hair cosmetic of the present invention may be produced by any method and can be prepared by an ordinary method. That is, the hair cosmetic can be prepared by mixing the components (A) to (D) and the above-mentioned optional components.

(7) Form of Use of Hair Cosmetic of the Present Invention

The hair cosmetic of the present invention can be used by putting it in a container, such as an aerosol container, a trigger container, an atomizer container, a bottle container, a tube container, and a pump container. In particular, the hair cosmetic can be uniformly applied to hair when it is contained in a container for spraying mist, which is preferred for achieving the effects of the present invention. The hair cosmetic can be used in various forms, such as liquid, emulsion, cream, gel, and mousse, by containing other components. In particular, an aqueous, solubilized, or alcohol-based liquid is preferred for achieving the effects of the present invention.

The hair cosmetic of the present invention may have any viscosity, and a viscosity at 25° C. of 1000 mPa·s or less is suitable for easy application to hair. The viscosity can be measured with, for example, a single cylinder rotational viscometer, Vismetron, manufactured by Shibaura Systems Co., Ltd.

EXAMPLES

The present invention will now be described in more detail by the following examples, but is not limited to these examples.

Note that the symbol "%" in the following examples means "mass %".

1 Production of (Meth)Acrylic Silicone-Based Graft Copolymer

Reference Production Example 1

4 g of dimethyl 2,2-azobis(2-methyl propionate) (V-601)$^{(Note\ 2)}$, 40 g of one end methacrylate-substituted dimethylpolysiloxane (X-24-8201)$^{(Note\ 3)}$, 31 g of ethyl acrylate (EA)(Note 4), 27 g of 2-hydroxyethyl methacrylate (HEMA)(Note 5), 4 g of 3-trimethylammonium propyl methacrylamide chloride (MAPTAC)(Note 6), and 50 g of isopropanol(Note 1) were added to 100 g of isopropanol (IPA)(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

The ratio of the added monomers is as follows.
MAPTAC:EA:HEMA:X-24-8201=2:31:27:40 (mass ratio)
(Note 1) IPA, manufactured by Kanto Chemical Co., Inc.
(Note 2) V-601, manufactured by Wako Pure Chemical Industries, Ltd.
(Note 3) X-24-8201, manufactured by Shin-Etsu Chemical Co., Ltd.
(Note 4) EA, manufactured by Kanto Chemical Co., Inc.
(Note 5) HEMA, manufactured by Kanto Chemical Co., Inc.
(Note 6) MAPTAC, manufactured by Evonik Degussa Japan Co., Ltd., 50% aqueous solution Reference Production Example 2

4 g of dimethyl 2,2-azobis(2-methyl propionate)(Note 2), 40 g of one end methacrylate-substituted dimethylpolysiloxane (X-22-174DX)(Note 7), 31 g of ethyl acrylate(Note 4), 27 g of 2-hydroxyethyl methacrylate(Note 5), 4 g of 3-trimethylammonium propyl methacrylamide chloride(Note 6), and 170 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 90 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-22-174DX=2:31:27:40 (mass ratio)
(Note 7) X-22-174DX, manufactured by Shin-Etsu Chemical Co., Ltd.

Reference Production Example 3

4 g of dimethyl 2,2-azobis(2-methyl propionate)(Note 2), 40 g of one end methacrylate-substituted dimethylpolysiloxane (X-22-174ASX)(Note 8), 31 g of ethyl acrylate(Note 4), 27 g of 2-hydroxyethyl methacrylate(Note 5), 4 g of 3-trimethylammonium propyl methacrylamide chloride(Note 6), and 50 g of isopropanol(Note 1) were added to 100 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 83 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-22-174ASX=2:31:27:40 (mass ratio)
(Note 8) X-22-174ASX, manufactured by Shin-Etsu Chemical Co., Ltd.

Reference Production Example 4

4 g of dimethyl 2,2-azobis(2-methyl propionate)(Note 2), 40.4 g of one end methacrylate-substituted dimethylpolysiloxane (X-24-8201)(Note 3), 27.3 g of ethyl acrylate(Note 4), 31.3 g of 2-hydroxyethyl methacrylate(Note 5), 2 g of 3-trimethylammonium propyl methacrylamide chloride(Note 6), and 50 g of isopropanol(Note 1) were added to 100 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=1:27.3:31.3:40.4 (mass ratio)

Reference Production Example 5

4 g of dimethyl 2,2-azobis(2-methyl propionate)(Note 2), 40 g of one end methacrylate-substituted dimethylpolysiloxane (X-24-8201)(Note 3), 26 g of ethyl acrylate(Note 4), 30 g of 2-hydroxyethyl methacrylate(Note 5), 8 g of 3-trimethylammonium propyl methacrylamide chloride(Note 6), and 120 g of isopropanol(Note 1) were added to 50 g of isopropanol(Note 1), while stirring, in a three-necked flask in a nitrogen atmosphere at 70° C. to 80° C. for 3 to 4 hours. Subsequently, 1 g of dimethyl 2,2-azobis(2-methyl propionate)(Note 2) dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 83 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=4:26:30:40 (mass ratio)

Reference Production Example 6

4 g of dimethyl 2,2-azobis(2-methyl propionate)[Note 2], 20 g of one end methacrylate-substituted dimethylpolysiloxane (X-24-8201)[Note 3], 41.5 g of ethyl acrylate[Note 4], 36.5 g of 2-hydroxyethyl methacrylate[Note 5], 4 g of 3-trimethylammonium propyl methacrylamide chloride[Note 6], and 50 g of isopropanol[Note 1] were added to 100 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=2:41.5:36.5:20 (mass ratio)

Reference Production Example 7

4 g of dimethyl 2,2-azobis(2-methyl propionate)[Note 2], 50 g of one end methacrylate-substituted dimethylpolysiloxane (X-24-8201)[Note 3], 23 g of ethyl acrylate[Note 4], 25 g of 2-hydroxyethyl methacrylate[Note 5], 4 g of 3-trimethylammonium propyl methacrylamide chloride[Note 6], and 100 g of isopropanol[Note 1] were added to 50 g of isopropanol[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in IPA was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 96 g of a transparent rubber-like product.

It was confirmed by infrared absorption spectrometry that the obtained rubber-like product was a desired (meth)acrylic silicone-based graft copolymer.

The ratio of the added monomers is as follows.
MAPTAC:EA:HEMA:X-24-8201=2:23:25:50 (mass ratio)

Reference Production Example 8

4 g of dimethyl 2,2-azobis(2-methyl propionate) (V-601)[Note 2], 40 g of one end methacrylate-substituted dimethylpolysiloxane (X-24-8201)[Note 3], 31 g of ethyl acrylate (EA)[Note 4], 27 g of 2-hydroxyethyl methacrylate (HEMA)[Note 5], 3.34 g of dimethyldiallylammonium chloride (DADMAC)[Note 9], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis (2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

The ratio of the added monomers is as follows.
DADMAC:EA:HEMA:X-24-8201=2:31:27:40 (mass ratio)
(Note 9) DADMAC, manufactured by Tokyo Chemical Industry Co., Ltd., 60% aqueous solution Reference Production Example 9

4 g of dimethyl 2,2-azobis(2-methyl propionate) (V-601)[Note 2], 40 g of one end methacrylate-substituted dimethylpolysiloxane (X-24-8201)[Note 3], 30 g of ethyl acrylate (EA)[Note 4], 27 g of 2-hydroxyethyl methacrylate (HEMA)[Note 5], 6 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 89 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=3:30:27:40 (mass ratio)

Reference Production Example 10

4 g of dimethyl 2,2-azobis(2-methyl propionate) (V-601)[Note 2], 30 g of one end methacrylate-substituted dimethylpolysiloxane (X-24-8201)[Note 3], 35 g of ethyl acrylate (EA)[Note 4], 32 g of 2-hydroxyethyl methacrylate (HEMA)[Note 5], 6 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=3:35:32:30 (mass ratio)

Reference Production Example 11

4 g of dimethyl 2,2-azobis(2-methyl propionate) (V-601)[Note 2], 30 g of one end methacrylate-substituted dimethylpolysiloxane (X-24-8201)[Note 3], 36 g of ethyl acrylate (EA)[Note 4], 32 g of 2-hydroxyethyl methacrylate (HEMA)[Note 5], 4 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-24-8201=2:36:32:30 (mass ratio)

Reference Production Example 12

4 g of dimethyl 2,2-azobis(2-methyl propionate) (V-601)[Note 2], 30 g of one end methacrylate-substituted dimethylpolysiloxane (X-24-8201)[Note 3], 37 g of ethyl acrylate (EA)[Note 4], 32 g of 2-hydroxyethyl methacrylate (HEMA)[Note 5], 2 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 90 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 10° C.

The ratio of the added monomers is as follows.
MAPTAC:EA:HEMA:X-24-8201=1:37:32:30 (mass ratio)

Reference Production Example 13

4 g of dimethyl 2,2-azobis(2-methyl propionate) (V-601)[Note 2], 30 g of one end methacrylate-substituted dimethylpolysiloxane (X-22-174DX)[Note 7], 36 g of ethyl acrylate (EA)[Note 4], 32 g of 2-hydroxyethyl methacrylate (HEMA)[Note 5], 4 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 86 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 11° C.

The ratio of the added monomers is as follows.
MAPTAC:EA:HEMA:X-22-174DX=2:36:32:30 (mass ratio)

Reference Production Example 14

4 g of dimethyl 2,2-azobis(2-methyl propionate) (V-601)[Note 2], 40 g of one end methacrylate-substituted dimethylpolysiloxane (X-24-8201)[Note 3], 16 g of ethyl acrylate (EA)[Note 4], 42 g of 2-hydroxyethyl methacrylate (HEMA)[Note 5], 2 g of 3-trimethylammonium propyl methacrylamide chloride (MAPTAC)[Note 6], and 50 g of isopropanol[Note 1] were added to 100 g of isopropanol (IPA)[Note 1], while stirring, in a three-necked flask in a nitrogen atmosphere at 70° C. to 80° C. for 3 to 4 hours. Subsequently, 1 g of dimethyl 2,2-azobis(2-methyl propionate)[Note 2] dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 91 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 30° C.

The ratio of the added monomers is as follows.
MAPTAC:EA:HEMA:X-24-8201=1:16.2:42.4:40.4 (mass ratio)

Reference Production Example 15

4 g of dimethyl 2,2-azobis(2-methyl propionate) (V-601)$^{(Note\ 2)}$, 40 g of one end methacrylate-substituted dimethylpolysiloxane (X-24-8201)$^{(Note\ 3)}$, 27 g of ethyl acrylate (EA)$^{(Note\ 4)}$, 31 g of 2-hydroxyethyl methacrylate (HEMA)$^{(Note\ 5)}$, 2 g of 3-trimethylammonium propyl methacrylamide chloride (MAPTAC)$^{(Note\ 6)}$ and 50 g of isopropanol$^{(Note\ 1)}$ were added to 100 g of isopropanol (IPA)$^{(Note\ 1)}$, while stirring, in a three-necked flask in a nitrogen atmosphere at 70° C. to 80° C. for 3 to 4 hours. Subsequently, 1 g of dimethyl 2,2-azobis(2-methyl propionate)$^{(Note\ 2)}$ dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 88 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is 15° C.

The ratio of the added monomers is as follows.
MAPTAC:EA:HEMA:X-24-8201=1:27.3:31.3:40.4 (mass ratio)

Reference Production Example 16

4 g of dimethyl 2,2-azobis(2-methyl propionate) (V-601)$^{(Note\ 2)}$, 20.2 g of one end methacrylate-substituted dimethylpolysiloxane (X-24-8201)$^{(Note\ 3)}$, 65.7 g of ethyl acrylate (EA)$^{(Note\ 4)}$, 13.1 g of 2-hydroxyethyl methacrylate (HEMA)$^{(Note\ 5)}$, 2 g of 3-trimethylammonium propyl methacrylamide chloride (MAPTAC)$^{(Note\ 6)}$, and 50 g of isopropanol$^{(Note\ 1)}$ were added to 100 g of isopropanol (IPA)$^{(Note\ 1)}$, while stirring, in a three-necked flask in a nitrogen atmosphere at 70° C. to 80° C. for 3 to 4 hours. Subsequently, 1 g of dimethyl 2,2-azobis(2-methyl propionate)$^{(Note\ 2)}$ dissolved in isopropanol was added to the resulting solution, and the obtained mixture was then reacted in a temperature range from 70° C. to 80° C. for 5 hours, so as to obtain a viscous solution. This solution was poured into purified water, so that a graft polymer was deposited and precipitated. Thereafter, the precipitate was separated by filtration, and was then dried at 80° C. under a reduced pressure, so as to obtain 87 g of a transparent rubber-like product.

It was confirmed by infrared absorption spectrometry that the obtained rubber-like product was a desired (meth)acrylic silicone-based graft copolymer (wherein, as a result of the infrared absorption spectrometry, the product was confirmed to be a polymer having dimethylpolysiloxane, an amide bond, an ester bond, an alkyl group, and a hydroxyl group).

In addition, the glass transition temperature (Tg) theoretically calculated from EA and HEMA is −10° C.

The ratio of the added monomers is as follows.
MAPTAC:EA:HEMA:X-24-8201=1:65.7:13.1:20.2 (mass ratio)

2 Preparation of Hair Cosmetic

1) Case of Using Polyalkylene Glycol as Component (D)

Example 1

Hair cosmetics having compositions shown in Tables 1 to 3 were prepared by the method shown below and were evaluated and judged for each of the "hair-setting property", "non-flaking", "hair-rearranging property", and "non-stickiness" by the evaluation method and criteria shown below. The results are also shown in Tables 1 to 3.

TABLE 1

| No. | Component classification | Component Name | Inventive product (%) | | | | | | | | | |
|---|---|---|---|---|---|---|---|---|---|---|---|---|
| | | | 1 | 2 | 3 | 4 | 5 | 6 | 7 | 8 | 9 | 10 |
| 1 | A | Polymer of Reference Production Example 1 | 2 | 2 | 0.05 | 0.3 | 6 | 2 | 2 | 2 | 2 | 2 |
| 2 | B | Polyvinyl pyrrolidone | 3 | 3 | 3 | 3 | 3 | 0.05 | 0.5 | 15 | — | — |
| 3 | B | (Vinyl pyrrolidone/vinyl acetate) copolymer (Note 1) | — | — | — | — | — | — | — | — | 3 | — |
| 4 | B | (Octylacrylamide/hydroxypropyl acrylate/butylaminoethyl methacrylate) copolymer (Note 2) | — | — | — | — | — | — | — | — | — | 3 |
| 5 | B | Polyurethane-14 | — | — | — | — | — | — | — | — | — | — |
| 6 | B | (Methacryloyloxyethyl-carboxybetaine/alkyl methacrylate) copolymer (Note 3) | — | — | — | — | — | — | — | — | — | — |

TABLE 1-continued

| No. | Component classification | Component Name | Inventive product 1 | 2 | 3 | 4 | 5 | 6 | 7 | 8 | 9 | 10 (%) |
|---|---|---|---|---|---|---|---|---|---|---|---|---|
| 7 | B | Polyquaternium-11 | — | — | — | — | — | — | — | — | — | — |
| 8 | B | Polyquaternium-51 | — | — | — | — | — | — | — | — | — | — |
| 9 | B | Polyquaternium-10 | — | — | — | — | — | — | — | — | — | — |
| 10 | | Na alginate | — | — | — | — | — | — | — | — | — | — |
| 11 | | Na carboxymethyl cellulose | — | — | — | — | — | — | — | — | — | — |
| 12 | | Carboxyvinyl polymer | — | — | — | — | — | — | — | — | — | — |
| 13 | C | Ethanol | 30 | balance | 30 | 30 | 30 | 30 | 30 | 30 | 30 | 30 |
| 14 | D1 | Polyethylene glycol (number-average molecular weight: 1000) | 3 | 3 | 3 | 3 | 3 | 3 | 3 | 3 | 3 | 3 |
| 15 | D1 | Polyethylene glycol (number-average molecular weight: 400) | — | — | — | — | — | — | — | — | — | — |
| 16 | D1 | Polyethylene glycol (number-average molecular weight: 6000) | — | — | — | — | — | — | — | — | — | — |
| 17 | D1 | Polyethylene glycol (number-average molecular weight: 20000) | — | — | — | — | — | — | — | — | — | — |
| 18 | | Polyethylene glycol (number-average molecular weight: 200) | — | — | — | — | — | — | — | — | — | — |
| 19 | | Polyethylene glycol (number-average molecular weight: 400000) | — | — | — | — | — | — | — | — | — | — |
| 20 | | Polyethylene glycol (number-average molecular weight: 2000000) | — | — | — | — | — | — | — | — | — | — |
| 21 | | Aminomethylpropanol | — | — | — | — | — | — | — | — | — | 0.6 |
| 22 | | Triethanolamine | — | — | — | — | — | — | — | — | — | — |
| 23 | | Purified water | balance | — | balance | balance | balance | balance | balance | balance | balance | balance |
| | Bulking agents used in inventive product 2 | | | | | | | | | | | |
| 24 | | Dimethyl ether | — | 25 | — | — | — | — | — | — | — | — |
| 25 | | Liquefied petroleum gas (LPG) | — | 25 | — | — | — | — | — | — | — | — |
| | | Content ratio (A)/(B) | 0.67 | 0.67 | 0.02 | 0.1 | 2 | 40 | 4 | 0.13 | 0.67 | 0.67 |
| Score | | Hair-setting property | 4 | 4.2 | 4 | 4 | 4.5 | 3 | 3 | 5 | 5 | 5 |
| | | Non-flaking | 5 | 5 | 3.5 | 4.5 | 5 | 5 | 5 | 3 | 4.5 | 4.5 |
| | | Hair-rearranging property | 4.5 | 4.5 | 3.5 | 4 | 5 | 4 | 4 | 3.5 | 4 | 4 |
| | | Non-stickiness | 5 | 5 | 4 | 4.5 | 5 | 3.5 | 4 | 4.5 | 4 | 4.5 |
| Judgment | | Hair-setting property | Excellent | Excellent | Excellent | Excellent | Excellent | Good | Good | Excellent | Excellent | Excellent |
| | | Non-flaking | Excellent | Excellent | Good | Excellent | Excellent | Excellent | Excellent | Good | Excellent | Excellent |
| | | Hair-rearranging property | Excellent | Excellent | Good | Excellent | Excellent | Excellent | Excellent | Good | Excellent | Excellent |
| | | Non-stickiness | Excellent | Excellent | Excellent | Excellent | Good | Excellent | Excellent | Good | Excellent | Excellent |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 2

| No. | Component classification | Component Name | Inventive product 11 | 12 | 13 | 14 | 15 | 16 | 17 | 18 | 19 (%) |
|---|---|---|---|---|---|---|---|---|---|---|---|
| 1 | A | Polymer of Reference Production Example 1 | 2 | 2 | 2 | 2 | 2 | 2 | 2 | 2 | 2 |
| 2 | B | Polyvinyl pyrrolidone | — | — | — | — | — | 3 | 3 | 3 | 3 |
| 3 | B | (Vinyl pyrrolidone/vinyl acetate) copolymer (Note 1) | — | — | — | — | — | — | — | — | — |
| 4 | B | (Octylacrylamide/hydroxypropyl acrylate/butylaminoethyl methacrylate) copolymer (Note 2) | — | — | — | — | — | — | — | — | — |
| 5 | B | Polyurethane-14 | 0.5 | — | — | — | — | — | — | — | — |
| 6 | B | (Methacryloyloxyethyl carboxybetaine/alkyl methacrylate) copolymer (Note 3) | — | 3 | — | — | — | — | — | — | — |

TABLE 2-continued

| | Component | | Inventive product (%) | | | | | | | | |
|---|---|---|---|---|---|---|---|---|---|---|---|
| No. | classification | Component Name | 11 | 12 | 13 | 14 | 15 | 16 | 17 | 18 | 19 |
| 7 | B | Polyquaternium-11 | — | — | 0.5 | — | — | — | — | — | — |
| 8 | B | Polyquaternium-51 | — | — | — | 0.05 | — | — | — | — | — |
| 9 | B | Polyquaternium-10 | — | — | — | — | 0.05 | — | — | — | — |
| 10 | | Na alginate | — | — | — | — | — | — | — | — | — |
| 11 | | Na carboxymethyl cellulose | — | — | — | — | — | — | — | — | — |
| 12 | | Carboxyvinyl polymer | — | — | — | — | — | — | — | — | — |
| 13 | C | Ethanol | 30 | 30 | 30 | 30 | 30 | 30 | 30 | 30 | 30 |
| 14 | D1 | Polyethylene glycol (number-average molecular weight: 1000) | 3 | 3 | 3 | 3 | 3 | — | — | — | — |
| 15 | D1 | Polyethylene glycol (number-average molecular weight: 400) | — | — | — | — | — | 3 | — | — | 1.5 |
| 16 | D1 | Polyethylene glycol (number-average molecular weight: 6000) | — | — | — | — | — | — | 3 | — | — |
| 17 | D1 | Polyethylene glycol (number-average molecular weight: 20000) | — | — | — | — | — | — | — | 3 | 1.5 |
| 18 | | Polyethylene glycol (number-average molecular weight: 200) | — | — | — | — | — | — | — | — | — |
| 19 | | Polyethylene glycol (number-average molecular weight: 400000) | — | — | — | — | — | — | — | — | — |
| 20 | | Polyethylene glycol (number-average molecular weight: 2000000) | — | — | — | — | — | — | — | — | — |
| 21 | | Aminomethylpropanol | — | — | — | — | — | — | — | — | — |
| 22 | | Triethanolamine | — | — | — | — | — | — | — | — | — |
| 23 | | Purified water | balance | balance | balance | balance | balance | balance | balance | balance | balance |
| Bulking agents used in inventive product 2 | | | | | | | | | | | |
| 24 | | Dimethyl ether | — | — | — | — | — | — | — | — | — |
| 25 | | Liquefied petroleum gas (LPG) | — | — | — | — | — | — | — | — | — |
| | | Content ratio (A)/(B) | 4 | 0.67 | 4 | 40 | 40 | 0.67 | 0.67 | 0.67 | 0.67 |
| Score | | Hair-setting property | 3 | 4.5 | 3.5 | 3 | 3 | 3.5 | 4.5 | 4.5 | 4.5 |
| | | Non-flaking | 5 | 3.5 | 4.5 | 5 | 5 | 5 | 5 | 5 | 5 |
| | | Hair-rearranging property | 4.5 | 3.5 | 4 | 3 | 3 | 4 | 4.5 | 4.5 | 4.5 |
| | | Non-stickiness | 4 | 4.5 | 4 | 4.5 | 5 | 5 | 4.5 | 4 | 5 |
| Judgment | | Hair-setting property | Good | Excellent | Good | Good | Good | Good | Excellent | Excellent | Excellent |
| | | Non-flaking | Excellent | Good | Excellent | Excellent | Excellent | Excellent | Excellent | Excellent | Excellent |
| | | Hair-rearranging property | Excellent | Good | Excellent | Good | Good | Excellent | Excellent | Excellent | Excellent |
| | | Non-stickiness | Excellent | Excellent | Excellent | Excellent | Excellent | Excellent | Excellent | Excellent | Excellent |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 3

| | Component | | Comparative product (%) | | | | | | | | | |
|---|---|---|---|---|---|---|---|---|---|---|---|---|
| No. | classification | Component Name | 1 | 2 | 3 | 4 | 5 | 6 | 7 | 8 | 9 | 10 |
| 1 | A | Polymer of Reference Production Example 1 | — | 2 | 2 | 2 | 2 | 2 | 2 | 2 | 2 | 2 |
| 2 | B | Polyvinyl pyrrolidone | 3 | — | 3 | 3 | 3 | 3 | 3 | — | — | — |
| 3 | B | (Vinyl pyrrolidone/vinyl acetate) copolymer (Note 1) | — | — | — | — | — | — | — | — | — | — |
| 4 | B | (Octylacrylamide/hydroxypropyl acrylate/butylaminoethyl methacrylate) copolymer (Note 2) | — | — | — | — | — | — | — | — | — | — |

TABLE 3-continued

| No. | Component classification | Component Name | Comparative product 1 | 2 | 3 | 4 | 5 | 6 | 7 | 8 | 9 | 10 (%) |
|---|---|---|---|---|---|---|---|---|---|---|---|---|
| 5 | B | Polyurethane-14 | — | — | — | — | — | — | — | — | — | — |
| 6 | B | (Methacryloyloxyethyl-carboxybetaine/alkyl methacrylate) copolymer (Note 3) | — | — | — | — | — | — | — | — | — | — |
| 7 | B | Polyquaternium-11 | — | — | — | — | — | — | — | — | — | — |
| 8 | B | Polyquaternium-51 | — | — | — | — | — | — | — | — | — | — |
| 9 | B | Polyquaternium-10 | — | — | — | — | — | — | — | — | — | — |
| 10 | | Na alginate | — | — | — | — | — | — | — | 0.05 | — | — |
| 11 | | Na carboxymethyl cellulose | — | — | — | — | — | — | — | — | 0.05 | — |
| 12 | | Carboxyvinyl polymer | — | — | — | — | — | — | — | — | — | 0.05 |
| 13 | C | Ethanol | 30 | 30 | — | 30 | 30 | 30 | 30 | 30 | 30 | 30 |
| 14 | D1 | Polyethylene glycol (number-average molecular weight: 1000) | 3 | 3 | 3 | — | — | — | — | 3 | 3 | 3 |
| 15 | D1 | Polyethylene glycol (number-average molecular weight: 400) | — | — | — | — | — | — | — | — | — | — |
| 16 | D1 | Polyethylene glycol (number-average molecular weight: 6000) | — | — | — | — | — | — | — | — | — | — |
| 17 | D1 | Polyethylene glycol (number-average molecular weight: 20000) | — | — | — | — | — | — | — | — | — | — |
| 18 | | Polyethylene glycol (number-average molecular weight: 200) | — | — | — | — | 3 | — | — | — | — | — |
| 19 | | Polyethylene glycol (number-average molecular weight: 400000) | — | — | — | — | — | 3 | — | — | — | — |
| 20 | | Polyethylene glycol (number-average molecular weight: 2000000) | — | — | — | — | — | — | 3 | — | — | — |
| 21 | | Aminomethylpropanol | — | — | — | — | — | — | — | — | — | — |
| 22 | | Triethanolamine | — | — | — | — | — | — | — | — | — | 0.05 |
| 23 | | Purified water | balance | balance | balance | balance | balance | balance | balance | balance | balance | balance |
| Bulking agents used in inventive product 2 | | | | | | | | | | | | |
| 24 | | Dimethyl ether | — | — | — | — | — | — | — | — | — | — |
| 25 | | Liquefied petroleum gas (LPG) | — | — | — | — | — | — | — | — | — | — |
| | | Content ratio (A)/(B) | — | — | 0.67 | 0.67 | 0.67 | 0.67 | 0.67 | — | — | — |
| Score | | Hair-setting property | 3.5 | 1.5 | Not dissolved | 3 | 3 | 4.5 | 5 | Separated | Separated | Separated |
| | | Non-flaking | 1 | 5 | | 2.5 | 3 | 4 | 4 | | | |
| | | Hair-rearranging property | 3.5 | 2.5 | | 2.5 | 2.5 | 4.5 | 4.5 | | | |
| | | Non-stickiness | 2.5 | 2.5 | | 5 | 5 | 1.5 | 1 | | | |
| Judgment | | Hair-setting property | Good | Poor | | Good | Good | Excellent | Excellent | | | |
| | | Non-flaking | Poor | Excellent | | Fair | Good | Excellent | Excellent | | | |
| | | Hair-rearranging property | Good | Fair | | Fair | Fair | Excellent | Excellent | | | |
| | | Non-stickiness | Fair | Fair | | Excellent | Excellent | Poor | Poor | | | |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

[Production Method]
(Inventive Products 1 and 3 to 19 and Comparative Products 1 to 10)
A: Components 1 to 23 were uniformly mixed.
B: Mixture A was packed in an atomizer container to provide each hair cosmetic.
(Inventive Product 2)
A: Components 1 to 23 were uniformly mixed.
B: Mixture A and components 24 and 25 were packed in an aerosol container to provide a hair cosmetic.
The resulting inventive products 1 to 19 all had a viscosity at 25° C. of 1000 mPa·s or less.

[Evaluation Method of Evaluation Items]
Twenty panelists who were specialized for evaluation of cosmetic products used the hair cosmetics of the inventive products and comparative products and evaluated for the "hair-setting property", "non-flaking", "hair-rearranging property", and "non-stickiness" to score each item on a 5-point scale in accordance with the following evaluation standard. The average of the scores of all the panelists was rounded to the nearest 0.5 by rounding off the digits 1 and 2 and rounding up the digits 3 and 4 at the first decimal place and similarly rounding off the digits 6 and 7 and rounding up the digits 8 and 9 at the first decimal place.

The evaluation standard when the hair cosmetics of the present invention were used are shown below. The evaluation was conducted on a 5-point scale by scoring 5 points when a very high effect was sensed and scoring 1 point when no effect was sensed.

| [Evaluation results]: | [Score] |
|---|---|
| <Evaluation standard>: hair-setting property | |
| Excellent hair-setting property is sensed: | 5 points |
| Good hair-setting property is sensed: | 4 points |
| Fair hair-setting property is sensed: | 3 points |
| Poor hair-setting property is sensed: | 2 points |
| No hair-setting property is sensed: | 1 point |
| <Evaluation standard>: non-flaking | |
| No flaking occurs: | 5 points |
| Flaking hardly occurs: | 4 points |
| Flaking slightly occurs: | 3 points |
| Flaking occurs: | 2 points |
| Flaking highly occurs: | 1 point |
| <Evaluation standard>: hair-rearranging property | |
| Excellent hair-rearranging property is sensed: | 5 points |
| Good hair-rearranging property is sensed: | 4 points |
| Fair hair-rearranging property is sensed: | 3 points |
| Poor hair-rearranging property is sensed: | 2 points |
| No hair-rearranging property is sensed: | 1 point |
| <Evaluation standard>: non-stickiness | |
| No stickiness is sensed: | 5 points |
| Stickiness is hardly sensed: | 4 points |
| Stickiness is slightly sensed: | 3 points |
| Stickiness is sensed: | 2 points |
| Stickiness is highly sensed: | 1 point |

Criteria of score

[Judgment]: Average of scores

E (Excellent): 4 points or more

G (good): 3 points or more and less than 4 points

F (fair): 2 points or more and less than 3 points

P (poor): less than 2 points

As is obvious from the results shown in Tables 1 to 3, the hair cosmetics of the inventive products 1 to 17 were excellent in all items of the "hair-setting property", "non-flaking", "hair-rearranging property", and "non-stickiness".

In contrast, in comparative product 1 produced without mixing component (A), the "non-flaking" was inferior, and the "non-stickiness" was also unsatisfactory. In comparative product 2 produced without mixing component (B), the "hair-setting property" was inferior, and the "hair-rearranging property" and the "non-stickiness" were also unsatisfactory. In comparative product 3 produced without mixing component (C), component (A) could not be uniformly dissolved in the hair cosmetic because of the absence of ethanol. In comparative product 4 produced without mixing component (D), the "non-flaking" and the "hair-rearranging property" were unsatisfactory.

In addition, comparative products 5 to 7 were not uniform hair cosmetics. In comparative products 8 to 10 containing anionic polymers instead of component (B), the anionic substances, such as Na alginate and Na carboxymethyl cellulose, reacted with component (A) during the production to generate insoluble substances and thereby caused separation.

Example 2

Hair Gel

| (Formulation) | (%) |
|---|---|
| 1 Polyvinyl pyrrolidone | 5.0 |
| 2 Polyurethane-14 | 2.0 |
| 3 (Meth)acrylic silicone-based graft copolymer of Reference Production Example 1 | 0.5 |
| 4 Polyoxyethylene hydrogenated castor oil isostearate | 0.2 |
| 5 Fragrance | 0.2 |
| 6 Hydroxypropyl methylcellulose | 0.5 |
| 7 Glycerin | 2.0 |
| 8 1,3-Butylene glycol | 2.0 |
| 9 Polyethylene glycol (number-average molecular weight: 6000) | 2.0 |
| 10 Para-oxybenzoic acid ester | 0.1 |
| 11 Phenoxyethanol | 0.1 |
| 12 Hydrolyzed soybean protein | 0.5 |
| 13 Glycine | 0.5 |
| 14 Ethanol | 30.0 |
| 15 Purified water | balance |

(Production Method)

A: Components 4, 5, and 14 were uniformly mixed.

B: Components other than the mixture A were heated and were uniformly mixed.

C: The mixtures A and B were mixed to prepare a hair gel.

The hair gel in Example 2 of the present invention achieved a hair-setting property without causing flaking, allowed hair-rearranging, and was excellent in non-stickiness.

Example 3

Hair Spray

| (Formulation) | |
|---|---|
| | (%) |
| Undiluted solution | |
| 1 Acrylamide/dimethylaminopropylacrylamide/methoxy PEG methacrylate copolymer | 5.0 |
| 2 (Meth)acrylic silicone-based graft copolymer of Reference Production Example 1 | 1.0 |
| 3 Polyethylene glycol (number-average molecular weight: 20000) | 3.0 |
| 4 Polyethylene glycol (number-average molecular weight: 400) | 1.0 |
| 5 Ethylhexyl methoxycinnamate | 1.0 |
| 6 Ethylhexyl salicylate | 1.0 |
| 7 Dimethyl polysiloxane (10 cs) | 2.0 |
| 8 Lavender oil | 1.0 |
| 9 Isopropanol | 2.0 |
| 10 Ethanol | balance |
| Gas | |
| 1 LPG | 60.0 |
| 2 Dimethyl ether | 40.0 |

(Production Method)

A: Components 1 to 10 were uniformly mixed.

B: 60 parts of the undiluted solution mixture A and 40 parts of the gas were packed in an aerosol container to provide a hair spray.

The hair spray in Example 3 of the present invention achieved a hair-setting property without causing flaking, allowed hair-rearranging, and was excellent in non-stickiness. The hair spray of Example 3 had a viscosity at 25° C. of 1000 mPa·s or less.

Example 4

Hair Mousse

| (Formulation) | |
|---|---|
| | (%) |
| Undiluted solution | |
| 1 Vinyl pyrrolidone/vinyl acetate copolymer | 2.0 |
| 2 (Meth)acrylic silicone-based graft copolymer of Reference Production Example 1 | 2.0 |
| 3 Polyethylene glycol (number-average molecular weight: 1000) | 2.0 |
| 4 Polyethylene glycol (number-average molecular weight: 2000000) | 1.0 |
| 5 Propylene glycol | 1.0 |
| 6 Polyoxyethylene sorbitan fatty acid ester | 0.2 |
| 7 Methylphenylpolysiloxane | 2.0 |
| 8 Stearyltrimethylammonium chloride | 0.2 |
| 9 *Sclerotium* gum | 0.2 |
| 10 Shea fat | 1.0 |
| 11 Ethanol | 2.0 |
| 12 Purified water | balance |
| Gas | |
| LPG | 100.0 |

(Production Method)

A: Components 1 to 12 were uniformly mixed.

B: 95 parts of the undiluted solution mixture A and parts of the gas were packed in an aerosol container to provide a hair mousse.

The hair mousse in Example 4 of the present invention achieved a hair-setting property without causing flaking, allowed hair-rearranging, and was excellent in non-stickiness. The undiluted solution of the hair mousse of Example 4 had a viscosity at 25° C. of 1000 mPa·s or less.

2) Case of Using Sugar Alcohol as Component (D)

Example 5

Hair cosmetics having compositions shown in Tables 4 to 6 were prepared by the method shown below and were evaluated and judged for each of the "hair-setting property", "non-flaking", "hair-rearranging property", and "non-stickiness" by the evaluation method and criteria shown below. The results are also shown in Tables 4 to 6.

TABLE 4

| | | | Inventive product (%) | | | | | | | | | |
|---|---|---|---|---|---|---|---|---|---|---|---|---|
| No. | Component classification | Component Name | 1 | 2 | 3 | 4 | 5 | 6 | 7 | 8 | 9 | 10 |
| 1 | A | Polymer of Reference Production Example 1 | 2 | 2 | 0.05 | 0.3 | 6 | 2 | 2 | 2 | 2 | 2 |
| 2 | B | Polyvinyl pyrrolidone | 3 | 3 | 3 | 3 | 3 | 0.05 | 0.5 | 15 | — | — |
| 3 | B | (Vinyl pyrrolidone/vinyl acetate) copolymer (Note 1) | — | — | — | — | — | — | — | — | 3 | — |
| 4 | B | (Octylacrylamide/hydroxypropyl acrylate/butylaminoethyl methacrylate) copolymer (Note 2) | — | — | — | — | — | — | — | — | — | 3 |
| 5 | B | Polyurethane-14 | — | — | — | — | — | — | — | — | — | — |
| 6 | B | (Methacryloyloxyethyl-carboxybetaine/alkyl methacrylate) copolymer (Note 3) | — | — | — | — | — | — | — | — | — | — |
| 7 | B | Polyquaternium-11 | — | — | — | — | — | — | — | — | — | — |
| 8 | B | Polyquaternium-51 | — | — | — | — | — | — | — | — | — | — |
| 9 | B | Polyquaternium-10 | — | — | — | — | — | — | — | — | — | — |
| 10 | | Na alginate | — | — | — | — | — | — | — | — | — | — |
| 11 | | Na carboxymethyl cellulose | — | — | — | — | — | — | — | — | — | — |
| 12 | | Carboxyvinyl polymer | — | — | — | — | — | — | — | — | — | — |
| 13 | C | Ethanol | 30 | balance | 30 | 30 | 30 | 30 | 30 | 30 | 30 | 30 |
| 19 | D2 | Maltitol | 5 | 5 | 5 | 5 | 5 | 5 | 5 | 5 | 5 | 5 |
| 15 | D2 | Sorbitol | — | — | — | — | — | — | — | — | — | — |
| 16 | D2 | Mannitol | — | — | — | — | — | — | — | — | — | — |
| 17 | D2 | Erythritol | — | — | — | — | — | — | — | — | — | — |
| 18 | | Glucose | — | — | — | — | — | — | — | — | — | — |
| 19 | | Aminomethylpropanol | — | — | — | — | — | — | — | — | — | 0.6 |
| 20 | | Triethanolamine | — | — | — | — | — | — | — | — | — | — |
| 21 | | Purified water | balance | — | balance | balance | balance | balance | balance | balance | balance | balance |
| Bulking agents used in inventive product 2 | | | | | | | | | | | | |
| 22 | | Dimethyl ether | — | 25 | — | — | — | — | — | — | — | — |
| 23 | | Liquefied petroleum gas (LPG) | — | 25 | — | — | — | — | — | — | — | — |
| | | Content ratio (A)/(B) | 0.67 | 0.67 | 0.02 | 0.1 | 2 | 40 | 4 | 0.13 | 0.67 | 0.67 |
| Score | | Hair-setting property | 4.5 | 4.7 | 4 | 4 | 4.5 | 3 | 3.5 | 5 | 5 | 5 |
| | | Non-flaking | 5 | 5 | 4.5 | 4.5 | 5 | 5 | 5 | 3 | 4 | 4 |

TABLE 4-continued

| No. | Component classification | Component Name | Inventive product 1 | 2 | 3 | 4 | 5 | 6 | 7 | 8 | 9 | 10 (%) |
|---|---|---|---|---|---|---|---|---|---|---|---|---|
| | | Hair-rearranging property | 4.5 | 4.5 | 3.5 | 4 | 5 | 4 | 4.5 | 3.5 | 4.5 | 4.5 |
| | | Non-stickiness | 4.5 | 4.5 | 4 | 4.5 | 3.5 | 4 | 4.5 | 3.5 | 4 | 4 |
| Judgment | | Hair-setting property | Excellent | Excellent | Excellent | Excellent | Excellent | Good | Good | Excellent | Excellent | Excellent |
| | | Non-flaking | Excellent | Excellent | Excellent | Excellent | Excellent | Excellent | Excellent | Good | Excellent | Excellent |
| | | Hair-rearranging property | Excellent | Excellent | Good | Excellent | Excellent | Excellent | Excellent | Good | Excellent | Excellent |
| | | Non-stickiness | Excellent | Excellent | Excellent | Excellent | Good | Excellent | Excellent | Good | Excellent | Excellent |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 5

| No. | Component classification | Component Name | Inventive product 11 | 12 | 13 | 14 | 15 (%) |
|---|---|---|---|---|---|---|---|
| 1 | A | Polymer of Reference Production Example 1 | 2 | 2 | 2 | 2 | 2 |
| 2 | B | Polyvinyl pyrrolidone | — | — | — | — | — |
| 3 | B | (Vinyl pyrrolidone/vinyl acetate) copolymer (Note 1) | — | — | — | — | — |
| 4 | B | (Octylacrylamide/hydroxypropyl acrylate/butylaminoethyl methacrylate) copolymer (Note 2) | — | — | — | — | — |
| 5 | B | Polyurethane-14 | 0.5 | — | — | — | — |
| 6 | B | (Methacryloyloxyethylcarboxybetaine/alkyl methacrylate) copolymer (Note 3) | — | 3 | — | — | — |
| 7 | B | Polyquaternium-11 | — | — | 0.5 | — | — |
| 8 | B | Polyquaternium-51 | — | — | — | 0.05 | — |
| 9 | B | Polyquaternium-10 | — | — | — | — | 0.05 |
| 10 | | Na alginate | — | — | — | — | — |
| 11 | | Na carboxymethyl cellulose | — | — | — | — | — |
| 12 | | Carboxyvinyl polymer | — | — | — | — | — |
| 13 | C | Ethanol | 30 | 30 | 30 | 30 | 30 |
| 14 | D2 | Maltitol | 5 | 5 | 5 | 5 | 5 |
| 15 | D2 | Sorbitol | — | — | — | — | — |
| 16 | D2 | Mannitol | — | — | — | — | — |
| 17 | D2 | Erythritol | — | — | — | — | — |
| 18 | | Glucose | — | — | — | — | — |
| 19 | | Aminomethylpropanol | — | — | — | — | — |
| 20 | | Triethanolamine | — | — | — | — | — |
| 21 | | Purified water | balance | balance | balance | balance | balance |
| Bulking agents used in inventive product 2 | | | | | | | |
| 22 | | Dimethyl ether | — | — | — | — | — |
| 23 | | Liquefied petroleum gas (LPG) | — | — | — | — | — |
| | | Content ratio (A)/(B) | 4 | 0.67 | 4 | 40 | 40 |
| Score | | Hair-setting property | 3.5 | 5 | 4 | 3.5 | 3.5 |
| | | Non-flaking | 5 | 3 | 4.5 | 5 | 5 |
| | | Hair-rearranging property | 5 | 3 | 4 | 3 | 3 |
| | | Non-stickiness | 4 | 4 | 3.5 | 4 | 4.5 |
| Judgment | | Hair-setting property | Good | Excellent | Excellent | Good | Good |
| | | Non-flaking | Excellent | Good | Excellent | Excellent | Excellent |
| | | Hair-rearranging property | Excellent | Good | Excellent | Good | Good |
| | | Non-stickiness | Excellent | Excellent | Good | Excellent | Excellent |

| No. | Component classification | Component Name | Inventive product 16 | 17 | 18 | 19 |
|---|---|---|---|---|---|---|
| 1 | A | Polymer of Reference Production Example 1 | 2 | 2 | 2 | 2 |
| 2 | B | Polyvinyl pyrrolidone | 3 | 3 | 3 | 3 |
| 3 | B | (Vinyl pyrrolidone/vinyl acetate) copolymer (Note 1) | — | — | — | — |

TABLE 5-continued (%)

| No. | Component classification | Component Name | | | | |
|---|---|---|---|---|---|---|
| 4 | B | (Octylacrylamide/hydroxypropyl acrylate/butylaminoethyl methacrylate) copolymer (Note 2) | — | — | — | — |
| 5 | B | Polyurethane-14 | — | — | — | — |
| 6 | B | (Methacryloyloxyethylcarboxybetaine/alkyl methacrylate) copolymer (Note 3) | — | — | — | — |
| 7 | B | Polyquaternium-11 | — | — | — | — |
| 8 | B | Polyquaternium-51 | — | — | — | — |
| 9 | B | Polyquaternium-10 | — | — | — | — |
| 10 | | Na alginate | — | — | — | — |
| 11 | | Na carboxymethyl cellulose | — | — | — | — |
| 12 | | Carboxyvinyl polymer | — | — | — | — |
| 13 | C | Ethanol | 30 | 30 | 30 | 30 |
| 14 | D2 | Maltitol | — | 2.5 | — | — |
| 15 | D2 | Sorbitol | 5 | 2.5 | — | — |
| 16 | D2 | Mannitol | — | — | 5 | — |
| 17 | D2 | Erythritol | — | — | — | 5 |
| 18 | | Glucose | — | — | — | — |
| 19 | | Aminomethylpropanol | — | — | — | — |
| 20 | | Triethanolamine | — | — | — | — |
| 21 | | Purified water | balance | balance | balance | balance |
| | | Bulking agents used in inventive product 2 | | | | |
| 22 | | Dimethyl ether | — | — | — | — |
| 23 | | Liquefied petroleum gas (LPG) | — | — | — | — |
| | | Content ratio (A)/(B) | 0.67 | 0.67 | 0.67 | 0.67 |
| Score | | Hair-setting property | 5 | 4.5 | 3 | 3.5 |
| | | Non-flaking | 4 | 4.5 | 5 | 5 |
| | | Hair-rearranging property | 4 | 4.5 | 3 | 3.5 |
| | | Non-stickiness | 4.5 | 4.5 | 5 | 4.5 |
| Judgment | | Hair-setting property | Excellent | Excellent | Good | Good |
| | | Non-flaking | Excellent | Excellent | Excellent | Excellent |
| | | Hair-rearranging property | Excellent | Excellent | Good | Good |
| | | Non-stickiness | Excellent | Excellent | Excellent | Excellent |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 6

(%)

| | | | Comparative product | | | |
|---|---|---|---|---|---|---|
| No. | Component classification | Component Name | 1 | 2 | 3 | 4 |
| 1 | A | Polymer of Reference Production Example 1 | — | 2 | 2 | 2 |
| 2 | B | Polyvinyl pyrrolidone | 3 | — | 3 | 3 |
| 3 | B | Vinyl pyrrolidone/vinyl acetate) copolymer (Note 1) | — | — | — | — |
| 4 | B | (Octylacrylamide/hydroxypropyl acrylate/butylaminoethyl methacrylate) copolymer (Note 2) | — | — | — | — |
| 5 | B | Polyurethane-14 | — | — | — | — |
| 6 | B | (Methacryloyloxyethylcarboxybetaine/alkyl methacrylate) copolymer (Note 3) | — | — | — | — |
| 7 | B | Polyquaternium-11 | — | — | — | — |
| 8 | B | Polyquaternium-51 | — | — | — | — |
| 9 | B | Polyquaternium-10 | — | — | — | — |
| 10 | | Na alginate | — | — | — | — |
| 11 | | Na carboxymethyl cellulose | — | — | — | — |
| 12 | | Carboxyvinyl polymer | — | — | — | — |
| 13 | C | Ethanol | 30 | 30 | — | 30 |
| 14 | D2 | Maltitol | 5 | 5 | 5 | — |
| 15 | D2 | Sorbitol | — | — | — | — |
| 16 | D2 | Mannitol | — | — | — | — |
| 17 | D2 | Erythritol | — | — | — | — |
| 18 | | Glucose | — | — | — | — |
| 19 | | Aminomethylpropanol | — | — | — | — |
| 20 | | Triethanolamine | — | — | — | — |
| 21 | | Purified water | balance | balance | balance | balance |

TABLE 6-continued (%)

| No. | Component classification | Component Name | | | | |
|---|---|---|---|---|---|---|
| | Bulking agents used in inventive product 2 | | | | | |
| 22 | | Dimethyl ether | — | — | — | — |
| 23 | | Liquefied petroleum gas (LPG) | — | — | — | — |
| | | Content ratio (A)/(B) | — | — | 0.67 | 0.67 |
| Score | | Hair-setting property | 4 | 2 | Not dissolved | 3 |
| | | Non-flaking | 1 | 5 | | 2.5 |
| | | Hair-rearranging property | 3.5 | 2.5 | | 2.5 |
| | | Non-stickiness | 2 | 2 | | 5 |
| Judgment | | Hair-setting property | Excellent | Fair | | Good |
| | | Non-flaking | Poor | Excellent | | Fair |
| | | Hair-rearranging property | Good | Fair | | Fair |
| | | Non-stickiness | Fair | Fair | | Excellent |

| | Component | | Comparative product | | | |
|---|---|---|---|---|---|---|
| No. | classification | Component Name | 5 | 6 | 7 | 8 |
| 1 | A | Polymer of Reference Production Example 1 | 2 | 2 | 2 | 2 |
| 2 | B | Polyvinyl pyrrolidone | 3 | — | — | — |
| 3 | B | Vinyl pyrrolidone/vinyl acetate) copolymer (Note 1) | — | — | — | — |
| 4 | B | (Octylacrylamide/hydroxypropyl acrylate/butylaminoethyl methacrylate) copolymer (Note 2) | — | — | — | — |
| 5 | B | Polyurethane-14 | — | — | — | — |
| 6 | B | (Methacryloyloxyethylcarboxybetaine/alkyl methacrylate) copolymer (Note 3) | — | — | — | — |
| 7 | B | Polyquaternium-11 | — | — | — | — |
| 8 | B | Polyquaternium-51 | — | — | — | — |
| 9 | B | Polyquaternium-10 | — | — | — | — |
| 10 | | Na alginate | — | 0.05 | — | — |
| 11 | | Na carboxymethyl cellulose | — | — | 0.05 | — |
| 12 | | Carboxyvinyl polymer | — | — | — | 0.05 |
| 13 | C | Ethanol | 30 | 30 | 30 | 30 |
| 14 | D2 | Maltitol | — | — | — | — |
| 15 | D2 | Sorbitol | — | — | — | — |
| 16 | D2 | Mannitol | — | — | — | — |
| 17 | D2 | Erythritol | — | — | — | — |
| 18 | | Glucose | 5 | — | — | — |
| 19 | | Aminomethylpropanol | — | — | — | — |
| 20 | | Triethanolamine | — | — | — | 0.05 |
| 21 | | Purified water | balance | balance | balance | balance |
| | Bulking agents used in inventive product 2 | | | | | |
| 22 | | Dimethyl ether | — | — | — | — |
| 23 | | Liquefied petroleum gas (LPG) | — | — | — | — |
| | | Content ratio (A)/(B) | 0.67 | — | — | — |
| Score | | Hair-setting property | 3 | Separated | Separated | Separated |
| | | Non-flaking | 2.5 | | | |
| | | Hair-rearranging property | 2.5 | | | |
| | | Non-stickiness | 4 | | | |
| Judgment | | Hair-setting property | Good | | | |
| | | Non-flaking | Fair | | | |
| | | Hair-rearranging property | Fair | | | |
| | | Non-stickiness | Excellent | | | |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

(Production Method)
(Inventive Products 1 and 3 to 19 and Comparative Products 1 to 8)

A: Components 1 to 21 were uniformly mixed.

B: The mixture A was packed in an atomizer container to provide each hair cosmetic.

(Inventive Product 2)

A: Components 1 to 21 were uniformly mixed.

B: The mixture A and components 22 and 23 were packed in an aerosol container to provide a hair cosmetic.

The resulting inventive products all had a viscosity at 25° C. of 1000 mPa·s or less.

As is obvious from the results shown in Tables 4 to 6, the hair cosmetics of the inventive products 1 to 19 were excellent in all items of the "hair-setting property", "non-flaking", "hair-rearranging property", and "non-stickiness".

In contrast, in comparative product 1 produced without mixing component (A), the "non-flaking" was inferior, and the "non-stickiness" was also unsatisfactory. In comparative product 2 produced without mixing component (B), the "hair-setting property" was inferior, and the "hair-rearranging property" and the "non-stickiness" were also unsatisfactory. In comparative product 3 produced without mixing component (C), component (A) could not be uniformly dissolved in the hair cosmetic because of the absence of ethanol. In comparative product 4 produced without mixing component (D), the "non-flaking" and the "hair-rearranging property" were unsatisfactory.

These results revealed that all of components (A) to (D) are essential for the present invention and that the effects of the present invention cannot be achieved if any of these components is lacked.

In comparative product 5 containing glucose instead of component (D), the non-flaking and the hair-rearranging property were inferior, which suggested that sugar alcohol is essential. In comparative products 6 to 8, anionic substances, such as Na alginate, Na carboxymethyl cellulose, and a carboxyvinyl polymer, reacted with component (A) during the production to generate insoluble substances and thereby caused separation. That is, it was demonstrated that nonionic, amphoteric, and cationic film-forming polymers are suitable for mixing with component (A).

Example 6

Hair Gel

| (Formulation) | (%) |
|---|---|
| 1 Polyvinyl pyrrolidone | 5.0 |
| 2 Polyurethane-14 | 2.0 |
| 3 (Meth)acrylic silicone-based graft copolymer of Reference Production Example 1 | 0.5 |
| 4 Polyoxyethylene hydrogenated castor oil isostearate | 0.2 |
| 5 Fragrance | 0.2 |
| 6 Hydroxypropyl methylcellulose | 0.5 |
| 7 Glycerin | 2.0 |
| 8 1,3-Butylene glycol | 2.0 |
| 9 Maltitol | 2.0 |
| 10 Para-oxybenzoic acid ester | 0.1 |
| 11 Phenoxyethanol | 0.1 |
| 12 Hydrolyzed soybean protein | 0.5 |
| 13 Glycine | 0.5 |
| 14 Ethanol | 30.0 |
| 15 Purified water | balance |

(Production Method)

A: Components 4, 5, and 14 were uniformly mixed.

B: Components other than the mixture A were heated and were uniformly mixed.

C: The mixtures A and B were mixed to prepare a hair gel.

The hair gel in Example 6 of the present invention achieved a hair-setting property without causing flaking, allowed hair-rearranging, and was excellent in non-stickiness.

Example 7

Hair Spray

| (Formulation) | (%) |
|---|---|
| Undiluted solution | |
| 1 Acrylamide /dimethylaminopropylacrylamide/ methoxy PEG methacrylate copolymer | 5.0 |
| 2 (Meth)acrylic silicone-based graft copolymer of Reference Production Example 1 | 1.0 |
| 3 Sorbitol | 1.0 |
| 4 Ethylhexyl methoxycinnamate | 1.0 |
| 5 Ethylhexyl salicylate | 1.0 |

-continued

| (Formulation) | (%) |
|---|---|
| 6 Dimethyl polysiloxane (10 cs) | 2.0 |
| 7 Lavender oil | 1.0 |
| 8 Isopropanol | 2.0 |
| 9 Ethanol | balance |
| Gas | |
| 1 LPG | 60.0 |
| 2 Dimethyl ether | 40.0 |

(Production Method)

A: Components 1 to 9 were uniformly mixed.

B: 60 parts of the undiluted solution mixture A and 40 parts of the gas were packed in an aerosol container to provide a hair spray.

The hair spray in Example 7 of the present invention achieved a hair-setting property without causing flaking, allowed hair-rearranging, and was excellent in non-stickiness. The hair spray of Example 7 had a viscosity at 25° C. of 1000 mPa·s or less.

Example 8

Hair Mousse

| (Formulation) | (%) |
|---|---|
| Undiluted solution | |
| 1 Vinyl pyrrolidone/vinyl acetate copolymer | 2.0 |
| 2 (Meth)acrylic silicone-based graft copolymer of Reference Production Example 1 | 2.0 |
| 3 Sorbitol | 2.0 |
| 4 Polyethylene glycol (average molecular weight: 2000000) | 1.0 |
| 5 Propylene glycol | 1.0 |
| 6 Polyoxyethylene sorbitan fatty acid ester | 0.2 |
| 7 Methylphenylpolysiloxane | 2.0 |
| 8 Stearyltrimethylammonium chloride | 0.2 |
| 9 *Sclerotium* gum | 0.2 |
| 10 Shea fat | 1.0 |
| 11 Ethanol | 2.0 |
| 12 Purified water | balance |
| Gas | |
| LPG | 100.0 |

(Production Method)

A: Components 1 to 12 were uniformly mixed.

B: 95 parts of the undiluted solution mixture A and parts of the gas were packed in an aerosol container to provide a hair mousse.

The hair mousse in Example 8 of the present invention achieved a hair-setting property without causing flaking, allowed hair-rearranging, and was excellent in non-stickiness. The undiluted solution of the hair mousse of Example 8 had a viscosity at 25° C. of 1000 mPa·s or less.

3) Case of Using Both Polyalkylene Glycol and Sugar Alcohol as Component (D)

Example 9

Hair cosmetics having compositions shown in Tables 7 to 9 were prepared by the method shown below and were evaluated and judged for each of the "non-flaking", "hair-rearranging property", "impartation of feeling of gloss to hair" and "fluffy feeling" by the evaluation method and criteria shown below. The results are also shown in Tables 7 to 9.

TABLE 7

| No. | Component classification | Component Name | Inventive product (%) 1 | 2 | 3 | 4 | 5 | 6 | 7 | 8 | 9 |
|---|---|---|---|---|---|---|---|---|---|---|---|
| 1 | A | Polymer of Reference Production Example 1 | 2 | 2 | 2 | 2 | 2 | 2 | 2 | 2 | 2 |
| 2 | B | Polyvinyl pyrrolidone | 3 | 3 | 3 | 3 | 3 | 3 | 3 | 3 | 3 |
| 3 | B | (Vinyl pyrrolidone/vinyl acetate) copolymer (Note 1) | — | — | — | — | — | — | — | — | — |
| 4 | B | (Octylacrylamide/hydroxypropyl acrylate/butylaminoethyl methacrylate) copolymer (Note 2) | — | — | — | — | — | — | — | — | — |
| 5 | B | Polyurethane-14 | — | — | — | — | — | — | — | — | — |
| 6 | B | (Methacryloyloxyethylcarboxybetaine/alkyl methacrylate) copolymer (Note 3) | — | — | — | — | — | — | — | — | — |
| 7 | B | Polyquaternium-11 | — | — | — | — | — | — | — | — | — |
| 8 | B | Polyquaternium-51 | — | — | — | — | — | — | — | — | — |
| 9 | B | Polyquaternium-10 | — | — | — | — | — | — | — | — | — |
| 10 | | Na alginate | | | | | | | | | |
| 11 | | Na carboxymethyl cellulose | — | — | — | — | — | — | — | — | — |
| 12 | | Carboxyvinyl polymer | — | — | — | — | — | — | — | — | — |
| 13 | C | Ethanol | 30 | 30 | 30 | 30 | 30 | 30 | 30 | 30 | 30 |
| 14 | D2 | Maltitol | 5 | 5 | 5 | 5 | 5 | — | — | — | 5 |
| 15 | D2 | Sorbitol | — | — | — | — | — | 5 | — | — | — |
| 16 | D2 | Mannitol | — | — | — | — | — | — | 5 | — | — |
| 17 | D2 | Erythritol | — | — | — | — | — | — | — | 5 | — |
| 18 | | Glucose | — | — | — | — | — | — | — | — | — |
| 14 | D1 | Polyethylene glycol (number-average molecular weight: 200) | 5 | — | — | — | — | 5 | 5 | 5 | 2 |
| 15 | D1 | Polyethylene glycol (number-average molecular weight: 400) | — | 5 | — | — | — | — | — | — | — |
| 16 | D1 | Polyethylene glycol (number-average molecular weight: 1000) | — | — | 5 | — | — | — | — | — | — |
| 17 | D1 | Polyethylene glycol (number-average molecular weight: 6000) | — | — | — | 5 | — | — | — | — | — |
| 18 | D1 | Polyethylene glycol (number-average molecular weight: 20000) | — | — | — | — | 5 | — | — | — | — |
| 21 | | Aminomethylpropanol | — | — | — | — | — | — | — | — | — |
| 22 | | Triethanolamine | — | — | — | — | — | — | — | — | — |
| 23 | | Purified water | balance | balance | balance | balance | balance | balance | balance | balance | balance |
| | | Content ratio: component (D1)/component (D2) | 1 | 1 | 1 | 1 | 1 | 1 | 1 | 1 | 0.4 |
| Score | | Non-flaking | 5 | 5 | 4.5 | 4 | 3.5 | 4 | 5 | 5 | 3.5 |
| | | Hair-rearranging property | 4.5 | 5 | 5 | 4.5 | 4 | 4 | 3.5 | 3.5 | 3.5 |
| | | Impartation of feeling of gloss to hair | 4.5 | 5 | 4.5 | 4.5 | 4 | 4.5 | 4.5 | 4.5 | 4 |
| | | Fluffy feeling | 5 | 4.5 | 4.5 | 4 | 3.5 | 5 | 3.5 | 3.5 | 5 |
| Judgment | | Non-flaking | Excellent | Excellent | Excellent | Excellent | Good | Excellent | Excellent | Excellent | Good |
| | | Hair-rearranging property | Excellent | Excellent | Excellent | Excellent | Excellent | Excellent | Good | Good | Good |
| | | Impartation of feeling of gloss to hair | Excellent | Excellent | Excellent | Excellent | Excellent | Excellent | Excellent | Excellent | Excellent |
| | | Fluffy feeling | Excellent | Excellent | Excellent | Excellent | Good | Excellent | Good | Good | Excellent |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 8

| No. | Component classification | Component Name | Inventive product (%) 10 | 11 | 12 | 13 | 14 | 15 | 16 | 17 |
|---|---|---|---|---|---|---|---|---|---|---|
| 1 | A | Polymer of Reference Production Example 1 | 2 | 2 | 2 | 2 | 2 | — | 2 | 2 |
| 2 | B | Polyvinyl pyrrolidone | 3 | — | — | — | — | — | — | — |
| 3 | B | (Vinyl pyrrolidone/vinyl acetate) copolymer (Note 1) | — | 3 | — | — | — | — | — | — |
| 4 | B | (Octylacrylamide/hydroxypropyl acrylate/butylaminoethyl methacrylate) copolymer (Note 2) | — | — | 3 | — | — | — | — | — |

TABLE 8-continued

| No. | Component classification | Component Name | Inventive product 10 | 11 | 12 | 13 | 14 | 15 | 16 | 17 |
|---|---|---|---|---|---|---|---|---|---|---|
| 5 | B | Polyurethane-14 | — | — | — | 0.5 | — | — | — | — |
| 6 | B | (Methacryloyloxyethylcarboxybetaine/alkyl methacrylate) copolymer (Note 3) | — | — | — | — | 3 | — | — | — |
| 7 | B | Polyquaternium-11 | — | — | — | — | — | 0.5 | — | — |
| 8 | B | Polyquaternium-51 | — | — | — | — | — | — | 0.05 | — |
| 9 | B | Polyquaternium-10 | — | — | — | — | — | — | — | 0.05 |
| 10 |  | Na alginate | — | — | — | — | — | — | — | — |
| 11 |  | Na carboxymethyl cellulose | — | — | — | — | — | — | — | — |
| 12 |  | Carboxyvinyl polymer | — | — | — | — | — | — | — | — |
| 13 | C | Ethanol | 30 | 30 | 30 | 30 | 30 | 30 | 30 | 30 |
| 14 | D2 | Maltitol | 2 | 5 | 5 | 5 | 5 | 5 | 5 | 5 |
| 15 | D2 | Sorbitol | — | — | — | — | — | — | — | — |
| 16 | D2 | Mannitol | — | — | — | — | — | — | — | — |
| 17 | D2 | Erythritol | — | — | — | — | — | — | — | — |
| 18 |  | Glucose | — | — | — | — | — | — | — | — |
| 14 | D1 | Polyethylene glycol (number-average molecular weight: 200) | 5 | 5 | 5 | 5 | 5 | 5 | 5 | 5 |
| 15 | D1 | Polyethylene glycol (number-average molecular weight: 400) | — | — | — | — | — | — | — | — |
| 16 | D1 | Polyethylene glycol (number-average molecular weight: 1000) | — | — | — | — | — | — | — | — |
| 17 | D1 | Polyethylene glycol (number-average molecular weight: 6000) | — | — | — | — | — | — | — | — |
| 18 | D1 | Polyethylene glycol (number-average molecular weight: 20000) | — | — | — | — | — | — | — | — |
| 21 |  | Aminomethylpropanol | — | — | 0.6 | — | — | — | — | — |
| 22 |  | Triethanolamine | — | — | — | — | — | — | — | — |
| 23 |  | Purified water | balance | balance | balance | balance | balance | balance | balance | balance |
|  | Content ratio: component (D1)/component (D2) |  | 2.5 | 1 | 1 | 1 | 1 | 1 | 1 | 1 |
| Score | Non-flaking |  | 5 | 5 | 5 | 5 | 4 | 4.5 | 5 | 5 |
|  | Hair-rearranging property |  | 4.5 | 4.5 | 4.5 | 5 | 4 | 3.5 | 3 | 3 |
|  | Impartation of feeling of gloss to hair |  | 4.5 | 4.5 | 4.5 | 4 | 3.5 | 4 | 4 | 4.5 |
|  | Fluffy feeling |  | 3.5 | 5 | 5 | 4 | 3.5 | 3 | 3 | 3 |
| Judgment | Non-flaking |  | Excellent | Excellent | Excellent | Excellent | Excellent | Excellent | Excellent | Excellent |
|  | Hair-rearranging property |  | Excellent | Excellent | Excellent | Excellent | Excellent | Good | Good | Good |
|  | Impartation of feeling of gloss to hair |  | Excellent | Excellent | Excellent | Excellent | Good | Excellent | Excellent | Excellent |
|  | Fluffy feeling |  | Good | Excellent | Excellent | Excellent | Good | Good | Good | Good |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

TABLE 9

| No. | Component classification | Component Name | Comparative product 1 | 2 | 3 | 4 | 5 |
|---|---|---|---|---|---|---|---|
| 1 | A | Polymer of Reference Production Example 1 | — | 2 | 2 | 2 | 2 |
| 2 | B | Polyvinyl pyrrolidone | 3 | — | — | — | — |
| 3 | B | (Vinyl pyrrolidone/vinyl acetate) copolymer (Note 1) | — | — | — | — | — |
| 4 | B | (Octylacrylamide/hydroxypropyl acrylate/butylaminoethyl methacrylate) copolymer (Note 2) | — | — | — | — | — |
| 5 | B | Polyurethane-14 | — | — | — | — | — |
| 6 | B | (Methacryloyloxyethylcarboxybetaine/alkyl methacrylate) copolymer (Note 3) | — | — | — | — | — |
| 7 | B | Polyquaternium-11 | — | — | — | — | — |
| 8 | B | Polyquaternium-51 | — | — | — | — | — |
| 9 | B | Polyquaternium-10 | — | — | — | — | — |
| 10 |  | Na alginate | — | — | 0.05 | — | — |
| 11 |  | Na carboxymethyl cellulose | — | — | — | 0.05 | — |
| 12 |  | Carboxyvinyl polymer | — | — | — | — | 005 |
| 13 | C | Ethanol | 30 | 30 | 30 | 30 | 30 |
| 14 | D2 | Maltitol | 5 | 5 | 5 | 5 | 5 |

TABLE 9-continued

| No. | Component classification | Component Name | Comparative product 1 | 2 | 3 | 4 | 5 (%) |
|---|---|---|---|---|---|---|---|
| 15 | D2 | Sorbitol | — | — | — | — | — |
| 16 | D2 | Mannitol | — | — | — | — | — |
| 17 | D2 | Erythritol | — | — | — | — | — |
| 18 | | Glucose | — | — | — | — | — |
| 14 | D1 | Polyethylene glycol (number-average molecular weight: 200) | 5 | 5 | 5 | 5 | 5 |
| 15 | D1 | Polyethylene glycol (number-average molecular weight: 400) | — | — | — | — | — |
| 16 | D1 | Polyethylene glycol (number-average molecular weight: 1000) | — | — | — | — | — |
| 17 | D1 | Polyethylene glycol (number-average molecular weight: 6000) | — | — | — | — | — |
| 18 | D1 | Polyethylene glycol (number-average molecular weight: 20000) | — | — | — | — | — |
| 21 | | Aminomethylpropanol | — | — | — | — | — |
| 22 | | Triethanolamine | — | — | — | — | 0.05 |
| 23 | | Purified water | balance | balance | balance | balance | balance |
| | | Content ratio: component (D1)/component (D2) | 1 | 1 | 1 | 1 | 1 |
| Score | | Non-flaking | 4 | 5 | Precipitation | Precipitation | Precipitation |
| | | Hair-rearranging property | 3.5 | 2.5 | | | |
| | | Impartation of feeling of gloss to hair | 1 | 2 | | | |
| | | Fluffy feeling | 1.5 | 2 | | | |
| Judgment | | Non-flaking | Excellent | Excellent | | | |
| | | Hair-rearranging property | Good | Fair | | | |
| | | Impartation of feeling of gloss to hair | Poor | Fair | | | |
| | | Fluffy feeling | Poor | Fair | | | |

(Note 1): Acorn KS (manufactured by Osaka Organic Chemical Industry Ltd.)
(Note 2): Amphomer KS (manufactured by Akzo Nobel N.V.)
(Note 3): Yukaformer R205 (manufactured by Dia Chemco Co., Ltd.)

(Production Method)

A: Components 1 to 23 were uniformly mixed.

B: The mixture A was packed in an atomizer container to provide each hair cosmetic.

[Evaluation Method of Evaluation Items]

Twenty panelists who were specialized for evaluation of cosmetic products used the hair cosmetics of the inventive products and comparative products and evaluated for the "non-flaking", "hair-rearranging property", "impartation of feeling of gloss to hair", and "fluffy feeling" to score each item on a 5-point scale in accordance with the following evaluation standard. The average of the scores of all the panelists was rounded to the nearest 0.5 by rounding off the digits 1 and 2 and rounding up the digits 3 and 4 at the first decimal place and similarly rounding off the digits 6 and 7 and rounding up the digits 8 and 9 at the first decimal place.

The evaluation standard when the hair cosmetics of the present invention were used are shown below. The evaluation was conducted on a 5-point scale by scoring 5 points when a very high effect was sensed and scoring 1 point when no effect was sensed.

| [Evaluation results]: | [Score] |
|---|---|
| <Evaluation standard>: non-flaking | |
| No flaking occurs: | 5 points |
| Flaking hardly occurs: | 4 points |
| Flaking slightly occurs: | 3 points |
| Flaking occurs: | 2 points |
| Flaking highly occurs: | 1 point |
| <Evaluation standard>: hair-rearranging property | |
| Excellent hair-rearranging property is sensed: | 5 points |
| Good hair-rearranging property is sensed: | 4 points |
| Fair hair-rearranging property is sensed: | 3 points |
| Poor hair-rearranging property is sensed: | 2 points |
| No hair-rearranging property is sensed: | 1 point |
| <Evaluation standard>: impartation of feeling of gloss to hair | |
| Excellent feeling of gloss is provided: | 5 points |
| Good feeling of gloss is provided: | 4 points |
| Fair feeling of gloss is provided: | 3 points |
| Poor feeling of gloss is provided: | 2 points |
| No feeling of gloss is provided: | 1 point |
| <Evaluation standard>: impartation of fluffy feeling to hair | |
| Excellent fluffy feeling is sensed: | 5 points |
| Good fluffy feeling is sensed: | 4 points |
| Fair fluffy feeling is sensed: | 3 points |
| Poor fluffy feeling is sensed: | 2 points |
| No fluffy feeling is sensed: | 1 point |

Criteria of score
[Judgment]: Average of scores
E (Excellent): 4 points or more
G (good): 3 points or more and less than 4 points
F (fair): 2 points or more and less than 3 points
P (poor): less than 2 points As is obvious from the results shown in Tables 7 to 9, the hair dressing cosmetics of the inventive products 1 to 17 were hair cosmetics excellent in all items of the "non-flaking", "hair-rearranging property", "impartation of feeling of gloss to hair", and "fluffy feeling".

In contrast, in comparative product 1 produced without mixing component (A), the "impartation of feeling of gloss to hair" and "fluffy feeling" were inferior. In comparative product 2 produced without mixing component (B), the "hair-setting property" was inferior, and the "hair-rearranging property" and the "impartation of feeling of gloss to hair" were also unsatisfactory.

In comparative products 3 to 5 containing anionic polymers instead of component (B), anionic substances, such as Na alginate and Na carboxymethyl cellulose, generated, together with component (A), insoluble substances during the production and thereby caused separation, and no uniform hair cosmetics were prepared.

Example 10

Hair Gel

| (Formulation) | (%) |
| --- | --- |
| 1 Polyvinyl pyrrolidone | 5.0 |
| 2 Polyurethane-14 | 2.0 |
| 3 (Meth)acrylic silicone-based graft copolymer of Reference Production Example 1 | 0.5 |
| 4 Polyoxyethylene hydrogenated castor oil isostearate | 0.2 |
| 5 Fragrance | 0.2 |
| 6 Hydroxypropyl methylcellulose | 0.5 |
| 7 Glycerin | 2.0 |
| 8 1,3-Butylene glycol | 2.0 |
| 9 Polyethylene glycol (number-average molecular weight: 6000) | 2.0 |
| 10 Sorbitol | 1.0 |
| 11 Para-oxybenzoic acid ester | 0.1 |
| 12 Phenoxyethanol | 0.1 |
| 13 Hydrolyzed soybean protein | 0.5 |
| 14 Glycine | 0.5 |
| 15 Ethanol | 30.0 |
| 16 Purified water | balance |

(Production Method)

A: Components 4, 5, and 15 were uniformly mixed.

B: Components other than the mixture A were heated and were uniformly mixed.

C: The mixtures A and B were mixed to prepare a hair gel.

The hair gel of Example 10 was excellent in the fluffy feeling, achieved a hair-rearranging property without causing flaking, and further was excellent in impartation of feeling of gloss to hair.

Example 11

Hair Spray

| (Formulation) | (%) |
| --- | --- |
| Undiluted solution | |
| 1 Acrylamide/dimethylaminopropylacrylamide/methoxy PEG methacrylate copolymer | 5.0 |
| 2 (Meth)acrylic silicone-based graft copolymer of Reference Production Example 1 | 1.0 |
| 3 Polyethylene glycol (number-average molecular weight: 20000) | 3.0 |
| 4 Polyethylene glycol (number-average molecular weight: 400) | 1.0 |
| 5 Maltitol | 1.0 |
| 6 Ethylhexyl methoxycinnamate | 1.0 |
| 7 Ethylhexyl salicylate | 1.0 |
| 8 Dimethyl polysiloxane (10 cs) | 2.0 |
| 9 Lavender oil | 1.0 |
| 10 Isopropanol | 2.0 |
| 11 Ethanol | balance |
| Gas | |
| 1 LPG | 60.0 |
| 2 Dimethyl ether | 40.0 |

(Production Method)

A: Components 1 to 11 were uniformly mixed.

B: 60 parts of the undiluted solution mixture A and 40 parts of the gas were packed in an aerosol container to provide a hair spray.

The hair spray of Example 11 was excellent in fluffy feeling, achieved a hair-rearranging property without causing flaking, and further was excellent in impartation of feeling of gloss to hair.

Example 12

Hair Mousse

| (Formulation) | (%) |
| --- | --- |
| Undiluted solution | |
| 1 Vinyl pyrrolidone/vinyl acetate copolymer | 2.0 |
| 2 (Meth)acrylic silicone-based graft copolymer of Reference Production Example 1 | 2.0 |
| 3 Polyethylene glycol (number-average molecular weight: 1000) | 2.0 |
| 4 Polyethylene glycol (number-average molecular weight: 2000000) | 1.0 |
| 5 Sorbitol | 1.0 |
| 6 Propylene glycol | 1.0 |
| 7 Polyoxyethylene sorbitan fatty acid ester | 0.2 |
| 8 Methylphenylpolysiloxane | 2.0 |
| 9 Stearyltrimethylammonium chloride | 0.2 |
| 10 *Sclerotium* gum | 0.2 |
| 11 Shea fat | 1.0 |
| 12 Ethanol | 2.0 |
| 13 Purified water | balance |
| Gas | |
| LPG | 100.0 |

(Production Method)

A: Components 1 to 13 were uniformly mixed.

B: 95 parts of the undiluted solution mixture A and 5 parts of the gas were packed in an aerosol container to provide a hair mousse.

The hair mousse of Example 12 was excellent in fluffy feeling, achieved a hair-rearranging property without causing flaking, and further was excellent in impartation of feeling of gloss to hair.

The invention claimed is:

1. A hair cosmetic comprising the following components (A) to (D):

(A) a (meth)acrylic silicone-based graft copolymer that is obtained by reacting the following radically polymerizable monomers (a), (b), (c), and (d) and is dissolved at a level of 50 mass % or more in 99.5% ethanol at 25° C.:

(a) a compound represented by the following formula (I):

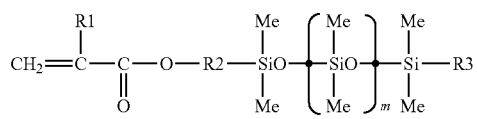

(wherein Me represents a methyl group, R1 represents a hydrogen atom or a methyl group, R2 represents a linear or branched divalent saturated hydrocarbon group containing 1 to 10 carbon atoms, which optionally comprises one or two ether bonds, R3 represents a saturated hydrocarbon group containing 1 to 10 carbon atoms, and m represents any of integer of 5 to 100);

(b) at least one selected from
a compound represented by the following formula (II):

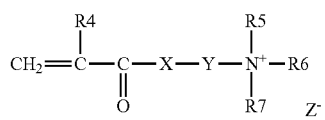

(wherein R4 represents a hydrogen atom or a methyl group, R5, R6 and R7, which are the same or different, each represents a hydrogen atom or an alkyl group containing 1 to 4 carbon atoms, X represents —O—, —NH—, —O—CH$_2$— or —O—CH$_2$CH(OH)—, Y represents a linear or branched divalent saturated hydrocarbon group containing 1 to 4 carbon atoms, and Z$^-$ represents a counter anion), and
a compound represented by the following formula (III):

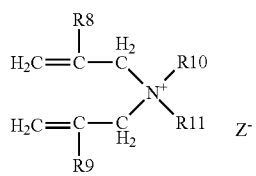

(wherein R8 and R9, which are the same or different, each represents a hydrogen atom or an alkyl group containing 1 to 4 carbon atoms, R10 and R11, which are the same or different, each represents a hydrogen atom or an alkyl group containing 1 to 18 carbon atoms, and Z$^-$ represents a counter anion);

(c) a compound represented by the following formula (IV):

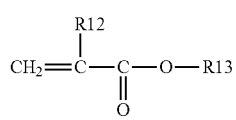

(wherein R12 represents a hydrogen atom or a methyl group, and R13 represents a hydrogen atom or a linear or branched alkyl group containing 1 to 3 carbon atoms); and (d) a compound represented by the following formula (V):

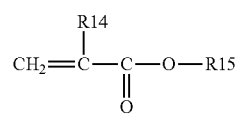

(wherein R14 represents a hydrogen atom or a methyl group, and R15 represents a hydroxyalkyl group containing 1 to 4 carbon atoms);

(B) at least one film-forming polymer selected from nonionic, amphoteric, and cationic polymers;

(C) a monohydric lower alcohol; and (D) at least one selected from polyalkylene glycols and sugar alcohols.

2. The hair cosmetic according to claim 1, wherein the component (B) is at least one selected from a polyvinyl pyrrolidone, a vinyl pyrrolidone/vinyl acetate copolymer, and a hydroxypropyl acrylate/butylaminoethyl methacrylate/octylamide acrylate copolymer.

3. The hair cosmetic according to claim 1, wherein the component (A) and the component (B) have a content ratio (A):(B) within a mass ratio range of 1:10 to 2:1.

4. The hair cosmetic according to claim 1, having a viscosity at 25° C. of 1000 mPa·s or less.

5. The hair cosmetic according to claim 3, having a viscosity at 25° C. of 1000 mPa·s or less.

6. The hair cosmetic according to claim 1, being contained in a container available for spraying the hair cosmetic as mist.

7. A cosmetic method comprising applying a composition comprising the following components (A) to (D) to hair:

(A) a (meth)acrylic silicone-based graft copolymer that is obtained by reacting the following radically polymerizable monomers (a), (b), (c), and (d) and is dissolved at a level of 50 mass % or more in 99.5% ethanol at 25° C.:

(a) a compound represented by the following formula (I):

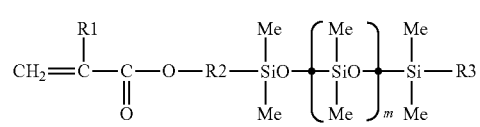

(wherein Me represents a methyl group, R1 represents a hydrogen atom or a methyl group, R2 represents a linear or branched divalent saturated hydrocarbon group containing 1 to 10 carbon atoms, which optionally comprises one or two ether bonds, R3 represents a saturated hydrocarbon group containing 1 to 10 carbon atoms, and m represents any of integer of 5 to 100);

(b) at least one selected from
a compound represented by the following formula (II):

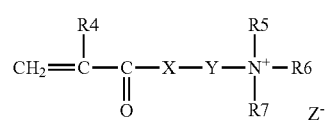

(wherein R4 represents a hydrogen atom or a methyl group, R5, R6 and R7, which are the same or different, each represents a hydrogen atom or an alkyl group containing 1 to 4 carbon atoms X represents —O—, —NH—, —O—CH$_2$— or —O—CH$_2$CH(OH)—, Y represents a linear or branched divalent saturated hydrocarbon group containing 1 to 4 carbon atoms, and Z$^-$ represents a counter anion), and a compound represented by the following formula (III):

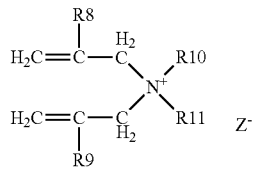
(III)

(wherein R8 and R9, which are the same or different, each represents a hydrogen atom or an alkyl group containing 1 to 4 carbon atoms, R10 and R11, which are the same or different, each represents a hydrogen atom or an alkyl group containing 1 to 18 carbon atoms, and Z$^-$ represents a counter anion);

(c) a compound represented by the following formula (IV):

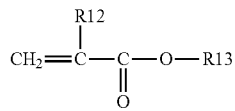
(IV)

(wherein R12 represents a hydrogen atom or a methyl group, and R13 represents a hydrogen atom or a linear or branched alkyl group containing 1 to 3 carbon atoms); and (d) a compound represented by the following formula (V):

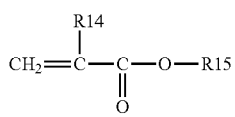
(V)

(wherein R14 represents a hydrogen atom or a methyl group, and R15 represents a hydroxyalkyl group containing 1 to 4 carbon atoms);

(B) at least one film-forming polymer selected from nonionic, amphoteric, and cationic polymers;

(C) a monohydric lower alcohol; and (D) at least one selected from polyalkylene glycols and sugar alcohols.

8. The cosmetic method according to claim 7, wherein the component (B) is at least one selected from a polyvinyl pyrrolidone, a vinyl pyrrolidone/vinyl acetate copolymer, and a hydroxypropyl acrylate/butylaminoethyl methacrylate/octylamide acrylate copolymer.

9. The cosmetic method according to claim 7, wherein the component (A) and the component (B) have a content ratio (A):(B) within a mass ratio range of 1:10 to 2:1.

10. The cosmetic method according to claim 7, wherein the composition has a viscosity at 25° C. of 1000 mPa·s or less.

11. The cosmetic method according to claim 9, wherein the composition has a viscosity at 25° C. of 1000 mPa·s or less.

12. The cosmetic method according to claim 7, wherein the composition is contained in a container available for spraying the hair cosmetic as mist.

* * * * *